(12) United States Patent
Shiono et al.

(10) Patent No.: US 7,648,816 B2
(45) Date of Patent: Jan. 19, 2010

(54) POSITIVE RESIST COMPOSITION, METHOD FOR FORMING RESIST PATTERN AND COMPOUND

(75) Inventors: Daiju Shiono, Kawasaki (JP); Taku Hirayama, Kawasaki (JP); Hideo Hada, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 164 days.

(21) Appl. No.: 11/817,012

(22) PCT Filed: Feb. 20, 2006

(86) PCT No.: PCT/JP2006/302961

§ 371 (c)(1),
(2), (4) Date: Aug. 23, 2007

(87) PCT Pub. No.: WO2006/090667

PCT Pub. Date: Aug. 31, 2006

(65) Prior Publication Data

US 2009/0035691 A1    Feb. 5, 2009

(30) Foreign Application Priority Data

Feb. 25, 2005    (JP)    ............... 2005-051219

(51) Int. Cl.
G03F 7/039 (2006.01)
G03F 7/20 (2006.01)
G03F 7/30 (2006.01)
C07C 39/04 (2006.01)

(52) U.S. Cl. ............... 430/270.1; 430/326; 430/905; 568/720; 568/721; 568/722

(58) Field of Classification Search ............... None
See application file for complete search history.

(56) References Cited

FOREIGN PATENT DOCUMENTS

| JP | 2001312055 | 11/2001 |
|---|---|---|
| JP | 2002099088 | 4/2002 |
| JP | 2002099089 | 4/2002 |
| JP | 2005266740 | 9/2005 |
| JP | 2006039281 | 2/2006 |

OTHER PUBLICATIONS

Machine-assisted English translation of JP 2006-39281 provided by JPO (2006).*
Machine-assisted English translation of JP 2005-266740 provided by JPO (2005).*
Machine-assisted English translation of JP 2001-312055 provided by JPO (2001).*
International Search Report from PCT/JP2006/302961, mailed Mar. 28, 2006.

* cited by examiner

*Primary Examiner*—Sin J. Lee
(74) *Attorney, Agent, or Firm*—Knobbe, Martens, Olson & Bear, LLP

(57) ABSTRACT

A positive resist composition that includes a base material component (A) that contains an acid-dissociable, dissolution-inhibiting group and exhibits increased alkali solubility under the action of acid, and an acid generator component (B) that generates acid upon exposure, wherein the base material component (A) contains a compound (A1), in which either a portion of, or all of, the hydrogen atoms of phenolic hydroxyl groups within a polyhydric phenol compound with a molecular weight of 300 to 2,500 represented by a general formula (I) shown below have been substituted with at least one group selected from the group consisting of acid-dissociable, dissolution-inhibiting groups represented by a general formula (II) shown below and acid-dissociable, dissolution-inhibiting groups represented by a general formula (III) shown below.

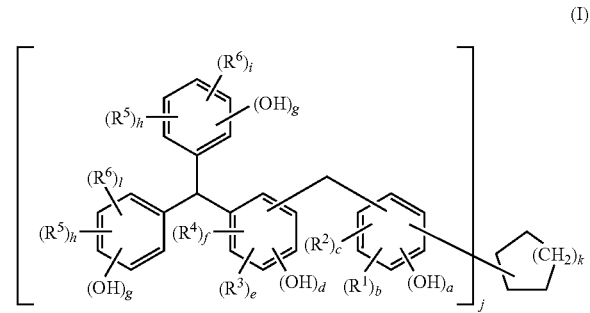

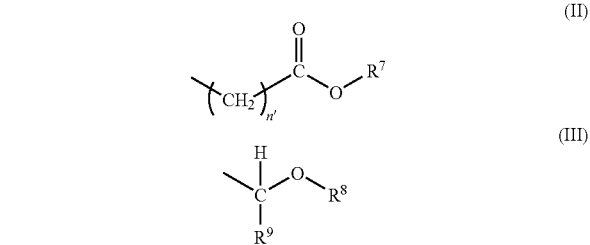

5 Claims, No Drawings

POSITIVE RESIST COMPOSITION, METHOD FOR FORMING RESIST PATTERN AND COMPOUND

RELATED APPLICATIONS

This application is the U.S. National Phase filing under 35 U.S.C. §371 of PCT/JP2006/302961, filed Feb. 20, 2006, which designated the United States and was published in a language other than English, which claims priority under 35 U.S.C. §119(a)-(d) to Japanese Patent Application No. 2005-051219, filed Feb. 25, 2005. The content of these applications is incorporated herein by reference in their entireties.

TECHNICAL FIELD

The present invention relates to a positive resist composition, a method for forming a resist pattern that uses the positive resist composition, and a compound that is ideal for use within the positive resist composition.

BACKGROUND ART

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultra violet radiation typified by g-line and i-line radiation has been used, but nowadays, mass production of semiconductor elements using KrF excimer lasers and ArF excimer lasers has commenced. Furthermore, investigation is also being conducted into radiation with even shorter wavelengths than these excimer lasers, including $F_2$ excimer lasers, electron beams, EUV (extreme ultra violet), and X-rays.

Furthermore, one example of a known pattern-forming material capable of forming a pattern of minute dimensions is a chemically amplified resist, which includes a base material component with a film-forming capability, and an acid generator component that generates an acid upon exposure. Chemically amplified resists include negative resists, which undergo a reduction in alkali solubility on exposure, and positive resists, which exhibit increased alkali solubility on exposure.

Conventionally, polymers have been used as the base material components within these types of chemically amplified resists, and examples of these polymers include polyhydroxystyrene (PHS), PHS-based resins in which a portion of the hydroxyl groups of PHS have been protected with acid-dissociable, dissolution-inhibiting groups, copolymers derived from (meth)acrylate esters, and resins in which a portion of the carboxyl groups within these (meth)acrylate esters have been protected with acid-dissociable, dissolution-inhibiting groups.

However, even for the pattern-forming materials described above, so long as a polymer is used as the base material component, the molecular size of the polymer becomes an impediment that makes further miniaturization of the resist pattern impossible.

In order to overcome this type of problem, resists have been proposed that employ a low molecular weight material as the base material component. For example, patent references 1 and 2 propose low molecular weight materials that include alkali-soluble groups such as hydroxyl groups, wherein either a portion of, or all of, these groups have been protected with acid-dissociable, dissolution-inhibiting groups.

[Patent Reference 1]
Japanese Unexamined Patent Application, First Publication No. 2002-099088
[Patent Reference 2]
Japanese Unexamined Patent Application, First Publication No. 2002-099089

DISCLOSURE OF INVENTION

However, using these low molecular weight materials, the formation of very fine patterns with dimensions of less than 90 nm at a level that enables their practical application has proven very difficult. Specific problems include an inability to form a pattern at all (an inferior pattern-forming capability), or even if a pattern is able to be formed, an inability to satisfactorily maintain the pattern shape (a low pattern retention capability).

The present invention takes the above circumstances into consideration, with an object of providing a positive resist composition and a method for forming a resist pattern that are capable of forming a very fine pattern with a high level of resolution, as well as providing a compound that is ideal for use within the positive resist composition.

As a result of intensive investigation, the inventors of the present invention discovered that a compound prepared by protecting the phenolic hydroxyl groups of a polyhydric phenol compound having a specific structure and a specific molecular weight with a specific acid-dissociable, dissolution-inhibiting group was able to achieve the object described above, and they were therefore able to complete the present invention.

In other words, a first aspect of the present invention is a positive resist composition that includes a base material component (A) that contains an acid-dissociable, dissolution-inhibiting group and exhibits increased alkali solubility under action of acid, and an acid generator component (B) that generates acid upon exposure, wherein the base material component (A) contains a compound (A1), in which either a portion of, or all of, hydrogen atoms of phenolic hydroxyl groups within a polyhydric phenol compound with a molecular weight of 300 to 2,500 represented by a general formula (I) shown below have been substituted with at least one group selected from the group consisting of acid-dissociable, dissolution-inhibiting groups represented by a general formula (II) shown below and acid-dissociable, dissolution-inhibiting groups represented by a general formula (III) shown below.

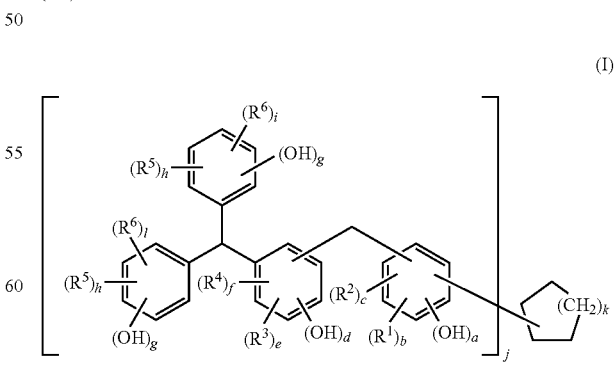

[In the formula (I), $R^1$ to $R^6$ each represent, independently, an alkyl group of 1 to 10 carbon atoms or an aromatic hydrocarbon group, which may include a hetero atom within the structure; a represents an integer of 1 or greater, and b and c each represent, independently, either 0 or an integer of 1 or greater, provided that at least one of b or c is an integer of 1 or greater, and a+b+c is no greater than 4; d represents an integer of 1 or greater, and e and f each represent, independently, either 0 or an integer of 1 or greater, provided that d+e+f is no greater than 4; g represents an integer of 1 or greater, and h and each represent, independently, either 0 or an integer of 1 or greater, provided that at least one of h or i is an integer of 1 or greater, and g+h+i is no greater than 4; j represents either 1 or 2; and k represents an integer from 1 to 3.]

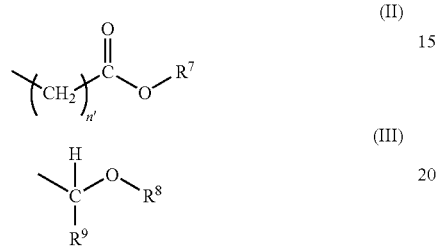

[In these formulas, $R^7$ and $R^8$ each represent, independently, a straight-chain, branched, or cyclic alkyl group, which may include a hetero atom within the structure; $R^9$ represents a hydrogen atom or a lower alkyl group; and n' represents an integer from 1 to 3.]

Furthermore, a second aspect of the present invention is a method for forming a resist pattern that includes the steps of: forming a resist film on a substrate using a positive resist composition according to the first aspect of the present invention described above, conducting exposure of the resist film, and developing the resist film to form a resist pattern.

Furthermore, a third aspect of the present invention is a compound, wherein either a portion of, or all of, hydrogen atoms of phenolic hydroxyl groups within a polyhydric phenol compound with a molecular weight of 300 to 2,500 represented by a general formula (I) shown below have been substituted with at least one group selected from the group consisting of acid-dissociable, dissolution-inhibiting groups represented by a general formula (II) shown below and acid-dissociable, dissolution-inhibiting groups represented by a general formula (III) shown below.

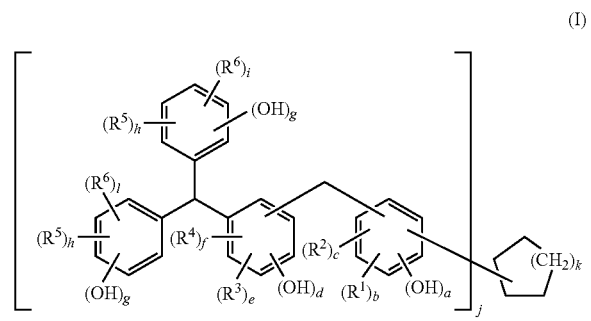

[In the formula (I), $R^1$ to $R^6$ each represent, independently, an alkyl group of 1 to 10 carbon atoms or an aromatic hydrocarbon group, which may include a hetero atom within the structure; a represents an integer of 1 or greater, and b and c each represent, independently, either 0 or an integer of 1 or greater, provided that at least one of b or c is an integer of 1 or greater, and a+b+c is no greater than 4; d represents an integer of 1 or greater, and e and f each represent, independently, either 0 or an integer of 1 or greater, provided that d+e+f is no greater than 4; g represents an integer of 1 or greater, and h and each represent, independently, either 0 or an integer of 1 or greater, provided that at least one of h or i is an integer of 1 or greater, and g+h+i is no greater than 4; j represents either 1 or 2; and k represents an integer from 1 to 3.]

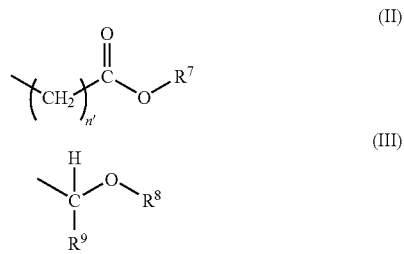

[In these formulas, $R^7$ and $R^8$ each represent, independently, a straight-chain, branched, or cyclic alkyl group, which may include a hetero atom within the structure; $R^9$ represents a hydrogen atom or a lower alkyl group; and n' represents an integer from 1 to 3.]

In the present invention, the term "exposure" is a general concept that includes irradiation with any form of radiation.

Furthermore, in the present invention, unless stated otherwise, the term "alkyl group" refers to a monovalent saturated hydrocarbon group.

According to the present invention, a positive resist composition and a method for forming a resist pattern are provided that are capable of forming very fine patterns with a high level of resolution, and a compound that is ideal for use within the positive resist composition is also provided.

BEST MODE FOR CARRYING OUT THE INVENTION

A compound of the present invention (hereafter referred to as the compound (A1)) is a compound in which either a portion of, or all of, the hydrogen atoms of phenolic hydroxyl groups within a polyhydric phenol compound (hereafter also referred to as the polyhydric phenol compound (I)) with a molecular weight of 300 to 2,500 represented by the general formula (I) shown above have been substituted with at least one group selected from the group consisting of acid-dissociable, dissolution-inhibiting groups represented by the general formula (II) shown above and acid-dissociable, dissolution-inhibiting groups represented by the general formula (III) shown above.

When the compound (A1) is blended into a resist composition together with an acid generator component (B) that generates acid upon exposure, the action of the acid generated from the acid generator component (B) by exposure causes the acid-dissociable, dissolution-inhibiting groups (II) or (III), or the combination of the acid-dissociable, dissolution-inhibiting groups (II) and (III), within the compound (A1) to dissociate, thereby causing the entire compound (A1) to shift from an alkali-insoluble state to an alkali-soluble state.

Polyhydric Phenol Compound (I)

In the general formula (I), $R^1$ to $R^6$ each represent, independently, an alkyl group of 1 to 10 carbon atoms or an aromatic hydrocarbon group, wherein the group may include a hetero atom within the structure.

An alkyl group of $R^1$ to $R^6$ is preferably a straight-chain or branched lower alkyl group of 1 to 5 carbon atoms, or a cyclic alkyl group of 5 to 6 carbon atoms. Examples of suitable lower alkyl groups include a methyl group, ethyl group, propyl group, isopropyl group, n-butyl group, isobutyl group, tert-butyl group, pentyl group, isopentyl group, and neopentyl group. Examples of suitable cyclic alkyl groups include a cyclohexyl group and cyclopentyl group.

An aromatic hydrocarbon group of $R^1$ to $R^6$ is preferably a group of 6 to 15 carbon atoms, and examples include a phenyl group, tolyl group, xylyl group, mesityl group, phenethyl group, and naphthyl group.

In those cases where the alkyl group or aromatic hydrocarbon group of $R^1$ to $R^6$ contains a hetero atom within the group structure, either a portion of, or all of, the hydrogen atoms within the alkyl group or aromatic hydrocarbon group may be substituted with a group that contains a hetero atom (including those cases where the hetero atom itself functions as the substituent group), or a portion of the carbon atoms of the alkyl group or aromatic hydrocarbon group may be substituted with a hetero atom. Examples of suitable hetero atoms include an oxygen atom, sulfur atom, nitrogen atom, and fluorine atom.

The above "group that contains a hetero atom" may be the hetero atom itself, or a group that contains the hetero atom and a carbon atom and/or hydrogen atom, such as an alkoxy group that contains a hetero atom.

Of these possibilities, in terms of achieving superior effects for the present invention, a lower alkyl group or a cyclic alkyl group is preferred, and a methyl group or cyclohexyl group is particularly preferred.

In the general formula (I), a represents an integer of 1 or greater, and b and c each represent, independently, either 0 or an integer of 1 or greater, provided that at least one of b or c is an integer of 1 or greater, and a+b+c is no greater than 4.

a is preferably an integer from 1 to 2, and is most preferably 1.

b is preferably either 0 or an integer from 1 to 3, even more preferably 0 or an integer from 1 to 2, even more preferably either 0 or 1, and is most preferably 1.

c is preferably either 0 or an integer from 1 to 3, even more preferably 0 or an integer from 1 to 2, even more preferably either 0 or 1, and is most preferably 0.

In the general formula (I), d represents an integer of 1 or greater, and e and f each represent, independently, either 0 or an integer of 1 or greater, provided that d+e+f is no greater than 4.

d is preferably an integer from 1 to 2, and is most preferably 1.

e is preferably either 0 or an integer from 1 to 2, even more preferably either 0 or 1, and is most preferably 0.

f is preferably either 0 or an integer from 1 to 2, even more preferably either 0 or 1, and is most preferably 0.

In the general formula (I), g represents an integer of 1 or greater, and h and i each represent, independently, either 0 or an integer of 1 or greater, provided that at least one of h or i is an integer of 1 or greater, and g+h+i is no greater than 4.

g is preferably an integer from 1 to 2, and is most preferably 1.

h is preferably either 0 or an integer from 1 to 2, even more preferably either 0 or 1, and is most preferably 1.

i is preferably either 0 or an integer from 1 to 2, even more preferably either 0 or 1, and is most preferably 1.

In the general formula (I), j represents either 1 or 2, and is preferably 2. In those cases where j=2, the two groups are preferably bonded to the same carbon atom of the cycloalkyl group. Furthermore, k represents an integer from 1 to 3. The case when k is 1 represents a group in which either one or two hydrogen atoms have been removed from cyclopentane, the case when k is 2 represents a group in which either one or two hydrogen atoms have been removed from cyclohexane, and the case when k is 3 represents a group in which either one or two hydrogen atoms have been removed from cycloheptane. k is most preferably 2.

As the polyhydric phenol compound (I), a compound represented by a formula (I-1) shown below (hereafter referred to as the polyhydric phenol compound (I-1)) is particularly preferred as it yields a high level of resolution and a favorable reduction in the level of roughness.

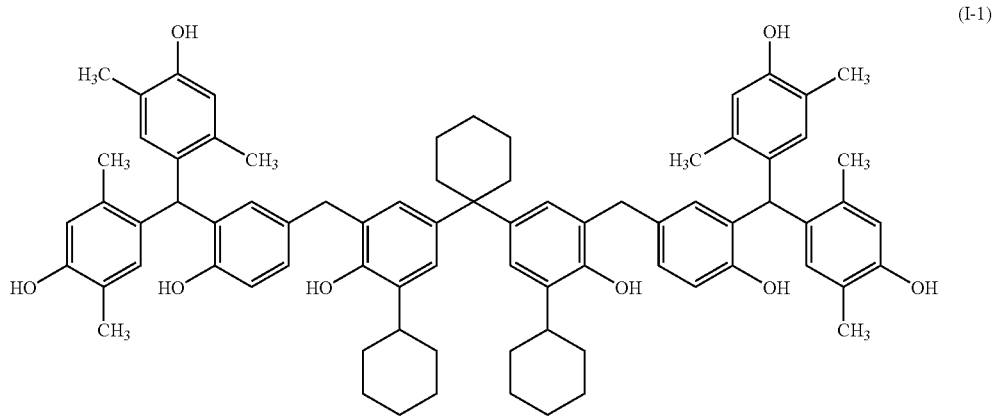

(I-1)

In the present invention, the molecular weight of the polyhydric phenol compound (I) must be within a range from 300 to 2,500, and this molecular weight is preferably from 450 to 1,500, and even more preferably from 500 to 1,200. By ensuring that the molecular weight falls within the above range, a pattern with excellent resolution can be formed. Furthermore, the level of roughness is also reduced, and the shape of the resist pattern profile is also very favorable.

Furthermore, if the molecular weight dispersity (Mw/Mn) for the polyhydric phenol compound (I) is no higher than 1.5, then the effects of the present invention are further enhanced. It is thought that the reason for this observation is that provided the polyhydric phenol compound (I) has a narrow molecular weight distribution in which the dispersity is no more than 1.5, then even if the positive resist composition includes, as the compound (A1), a plurality of compounds in which different numbers of phenolic hydroxyl group hydrogen atoms have been substituted with acid-dissociable, dissolution-inhibiting groups (namely, different protection numbers), the alkali solubility of each of these compounds will still be comparatively uniform. Smaller dispersity values are preferred, and the dispersity value is even more preferably no more than 1.4, and is most preferably 1.3 or smaller.

Dispersity values are usually used for polydisperse compounds such as polymers, but even for monodisperse compounds, the existence of impurities such as production by-products or residual starting materials can result in the appearance of an apparent molecular weight distribution when analysis is conducted using gel permeation chromatography (GPC) or the like. In other words, in the case of a monodisperse compound, a dispersity of 1 indicates a degree of purity of 100%, and increasingly large dispersity values indicate larger quantities of impurities.

In the present invention, the molecular weight dispersity is calculated for compounds that exhibit the above type of apparent molecular weight distribution by measuring the weight average molecular weight (Mw) and the number average molecular weight (Mn) using a typical method used for the measurement of these Mw and Mn values for a polymer, such as a GPC method, and then determining the Mw/Mn ratio.

The dispersity of the polyhydric phenol compound (I) can be adjusted either by removing reaction by-products and impurities following synthesis of the polyhydric phenol compound (I) that represents the targeted product, or by using conventional methods such as molecular weight fractionation treatments to remove the unneeded molecular weight fractions.

Furthermore, in the state where none of the phenolic hydroxyl group hydrogen atoms have been substituted with acid-dissociable, dissolution-inhibiting groups, the polyhydric phenol compound (I) must be a material that is capable of forming an amorphous (non-crystalline) film using a spin coating method.

Spin coating is one of the most commonly used methods for forming thin films, whereas an amorphous film refers to an optically transparent film that does not crystallize.

A judgment as to whether or not the polyhydric phenol compound (I) is capable of forming an amorphous film using spin coating is determined on the basis of whether or not a film formed by spin coating the compound onto an 8-inch silicon wafer is transparent across the entire film surface. More specifically, judgment can be conducted, for example, in the manner described below. First, the polyhydric phenol compound (I) is added to a solvent typically used as a resist solvent, such as a mixed solvent of ethyl lactate and propylene glycol monoethyl ether acetate in a ratio (weight ratio) of 40/60 (hereafter this solvent is abbreviated as EM), in sufficient quantity to generate a solution with a concentration of 14% by weight, and dissolution is achieved by ultrasound treatment (dissolution treatment) using an ultrasound cleaning apparatus. Subsequently, the resulting solution is spin coated onto a wafer at 1,500 rpm and subjected to optional drying and baking (PAB: Post Applied Bake) at 110° C. for 90 seconds, and a visual judgment is then made as to whether the formed film is transparent. If the film is transparent, then an amorphous film is deemed to have been formed. A non-transparent, cloudy film is not an amorphous film.

Moreover, the polyhydric phenol compound (I) preferably exhibits favorable stability for the amorphous film formed in the manner described above. For example, compounds for which the transparent state, namely the amorphous state, of the film is retained even after standing for 2 weeks at room temperature following the above PAB treatment are particularly desirable.

The polyhydric phenol compound (I) can be produced, for example, in the manner summarized below.

First, a bis-salicylaldehyde derivative and a phenol derivative (4 equivalents relative to the bis-salicylaldehyde derivative) are dissolved in an organic solvent, and the polyhydric phenol compound (I) can then be synthesized by reaction under acid conditions.

Acid-Dissociable, Dissolution-Inhibiting Group (II)

In the general formula (II), $R^7$ represents a straight-chain, branched, or cyclic alkyl group, wherein the alkyl group may include a hetero atom within the structure. In other words, in an alkyl group represented by $R^7$, either a portion of, or all of, the hydrogen atoms may be substituted with a group that contains a hetero atom (including those cases where the hetero atom itself functions as the substituent group), or a portion of the carbon atoms of the alkyl group may be substituted with a hetero atom. Examples of suitable hetero atoms include an oxygen atom, sulfur atom, nitrogen atom, and fluorine atom. The "group that contains a hetero atom" is as defined above.

Examples of alkyl groups in which either a portion of, or all of, the hydrogen atoms have been substituted with a hetero atom include fluorinated lower alkyl groups of 1 to 5 carbon atoms in which either a portion of, or all of, the hydrogen atoms have been substituted with fluorine atoms, groups in which two hydrogen atoms bonded to the same carbon atom have been substituted with a single oxygen atom (namely, groups containing a carbonyl group (C=O)), and groups in which two hydrogen atoms bonded to the same carbon atom have been substituted with a single sulfur atom (namely, groups containing a thiocarbonyl group (C=S)).

Examples of groups in which a portion of the carbon atoms of an alkyl group have been substituted with a hetero atom include examples in which a carbon atom has been substituted with a nitrogen atom (for example, branched or cyclic alkyl groups containing a —$CH_2$— group within the structure, wherein the —$CH_2$— has been substituted with a —NH— group), and examples in which a carbon atom has been substituted with an oxygen atom (for example, branched or cyclic alkyl groups containing a —$CH_2$— group within the structure, wherein the —$CH_2$— has been substituted with a —O— group).

n' represents an integer from 1 to 3, and is most preferably 1.

A straight-chain alkyl group represented by $R^7$ preferably contains from 1 to 5 carbon atoms, specific examples include a methyl group, ethyl group, n-propyl group, n-butyl group, isobutyl group and n-pentyl group, and a methyl group or ethyl group is preferred.

A branched alkyl group represented by $R^7$ preferably contains from 4 to 10 carbon atoms, and even more preferably from 4 to 8 carbon atoms. Specific examples include an isobutyl group, tert-butyl group, isopentyl group, neopentyl group and tert-pentyl group, and a tert-butyl group is preferred.

A cyclic alkyl group represented by $R^7$ preferably contains from 3 to 20 carbon atoms, even more preferably from 4 to 14 carbon atoms, and most preferably from 5 to 12 carbon atoms. The basic ring structure within the cyclic alkyl group (the basic ring excluding substituent groups) may be either monocyclic or polycyclic, although a polycyclic structure yields particularly superior effects for the present invention and is consequently preferred. Furthermore, the basic ring structure may be either a hydrocarbon ring formed solely from carbon and hydrogen, or a heterocycle in which a portion of the carbon atoms that constitute a hydrocarbon ring have been substituted with hetero atoms. In the present invention, groups in which the basic ring structure is a hydrocarbon ring are preferred. Examples of the hydrocarbon ring include monocycloalkanes, bicycloalkanes, tricycloalkanes, and tetracycloalkanes. Specific examples include monocycloalkanes such as cyclopentane and cyclohexane, and polycycloalkanes such as adamantane, norbornane, isobornane, tricyclodecane, and tetracyclododecane. Of these, adamantane, norbornane, tricyclodecane and tetracyclododecane are preferred, and adamantane is particularly desirable.

These basic ring structures may either contain a substituent group on the ring, or may contain no substituent groups. Examples of suitable substituent groups include lower alkyl groups, a fluorine atom, fluorinated lower alkyl groups, and an oxygen atom (=O). Suitable lower alkyl groups include straight-chain or branched alkyl groups of 1 to 5 carbon atoms such as a methyl group or ethyl group. In those cases where the basic ring structure contains a substituent group, the number of substituent groups is preferably within a range from 1 to 3, and is most preferably 1. The expression "contains a substituent group" means that a hydrogen atom bonded to a carbon atom that constitutes part of the basic ring structure has been substituted with a substituent group.

A cyclic alkyl group of $R^7$ is a group in which one hydrogen atom has been removed from the above type of basic ring structure. In the $R^7$ group, the carbon atom bonded to the oxygen atom adjacent to the $R^7$ group is preferably one of the carbon atoms that constitute the above type of basic ring structure, and compounds in which the carbon atom bonded to the oxygen atom adjacent to the $R^7$ group is a tertiary carbon atom to which a substituent group such as a lower alkyl group is also bonded yield particularly superior effects for the present invention and are consequently preferred. Examples of acid-dissociable, dissolution-inhibiting groups (II) that contain an aforementioned cyclic alkyl group as $R^7$ include the groups represented by the formulas shown below.

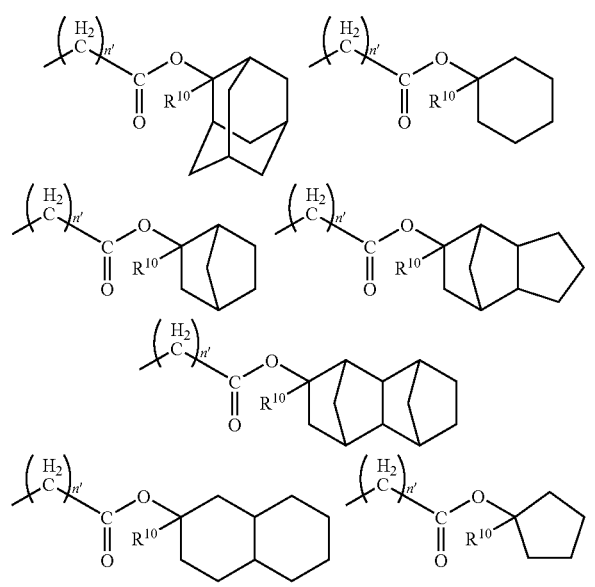

[wherein, $R^{10}$ represents a lower alkyl group, and n' is as defined above]

Of these, groups represented by a general formula (II-1) shown below are particularly preferred.

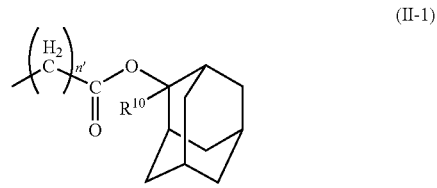

(II-1)

[wherein, $R^{10}$ and n' are as defined above]

A lower alkyl group represented by $R^{10}$ is an alkyl group of 1 to 5 carbon atoms, and specific examples of suitable groups include straight-chain or branched lower alkyl groups such as a methyl group, ethyl group, propyl group, isopropyl group, n-butyl group, isobutyl group, tert-butyl group, pentyl group, isopentyl group, and neopentyl group. In terms of industrial availability, $R^{10}$ is preferably a methyl group or ethyl group, and a methyl group is particularly desirable.

As the acid-dissociable, dissolution-inhibiting group (II), a group of the general formula (II) in which n' is 1 and $R^7$ is a tert-butyl group, or a group of the general formula (II-1) in which n' is 1 and $R^{10}$ is a methyl group is preferred, as these groups yield superior effects for the present invention.

Acid-Dissociable, Dissolution-Inhibiting Group (III)

Examples of the $R^8$ group within the general formula (III) include the same groups described above for the $R^7$ group. Of these, a straight-chain alkyl group or cyclic alkyl group is particularly preferred as the $R^8$ group.

The $R^9$ group within the general formula (III) represents a hydrogen atom or a lower alkyl group. A lower alkyl group represented by $R^9$ is an alkyl group of 1 to 5 carbon atoms, and specific examples of suitable groups include straight-chain or branched lower alkyl groups such as a methyl group, ethyl group, propyl group, isopropyl group, n-butyl group, isobutyl group, tert-butyl group, pentyl group, isopentyl group, and neopentyl group. In terms of industrial availability, $R^9$ is preferably a hydrogen atom or a methyl group, and a hydrogen atom is particularly desirable.

Examples of acid-dissociable, dissolution-inhibiting groups (III) in which the $R^8$ group is a straight-chain alkyl group include a 1-ethoxyethyl group, 1-ethoxymethyl group, 1-methoxyethyl group, 1-methoxymethyl group, 1-methoxypropyl group, 1-ethoxypropyl group, 1-n-butoxyethyl group, 1-pentafluoroethoxyethyl group, 1-trifluoromethoxyethyl group, and 1-trifluoromethoxymethyl group.

Examples of acid-dissociable, dissolution-inhibiting groups (III) in which the $R^8$ group is a cyclic alkyl group include groups of the formulas shown below.

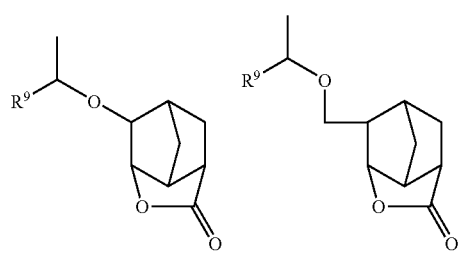

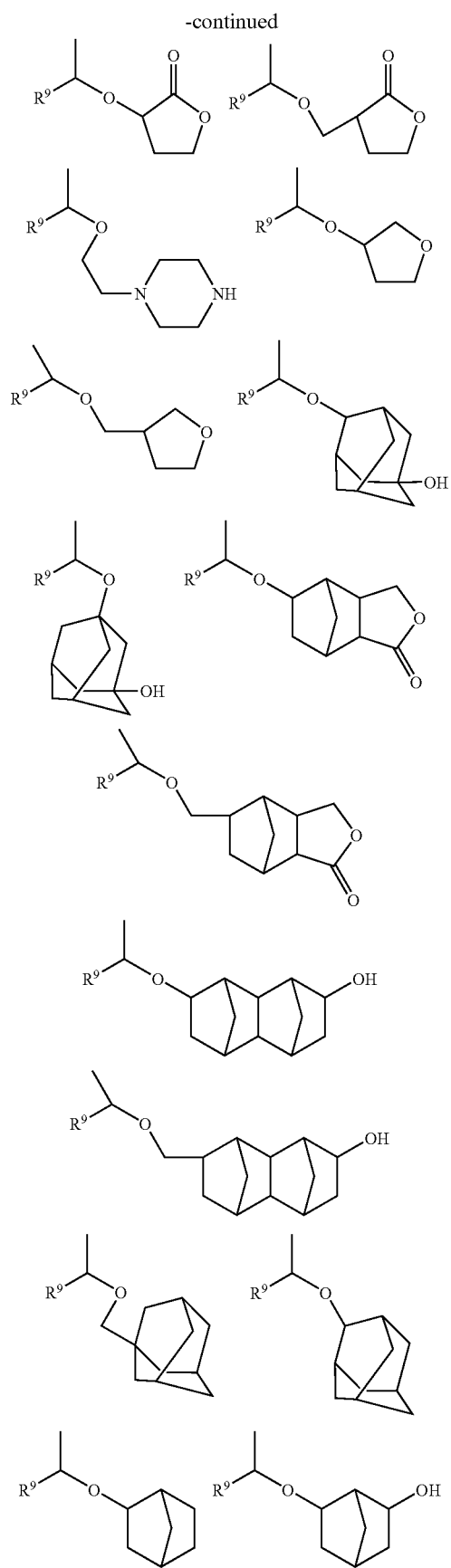

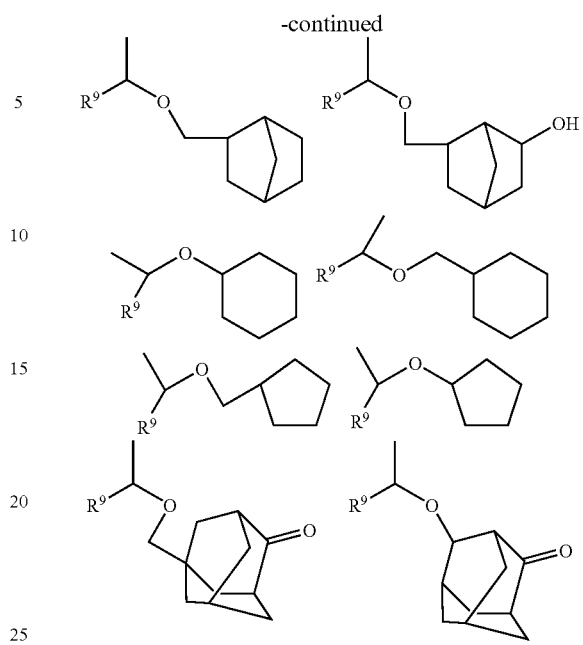

[wherein, $R^9$ is as defined above]

Of these, compounds (groups) represented by the general formula shown below are particularly preferred.

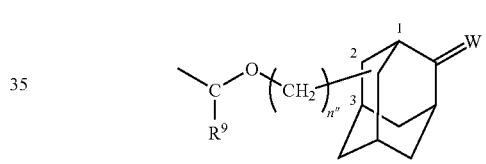

[wherein, $R^9$ is as defined above, n″ represents either 0 or an integer from 1 to 2, and W represents either two hydrogen atoms or an oxygen atom]

n″ is most preferably either 0 or 1. There are no particular restrictions on the bonding position between the adamantyl group and the —C($R^9$)—O—(CH$_2$)$_{n″}$— group, although bonding at either position 1 or position 2 of the adamantyl group is preferred.

In the compound (A1), the substituent groups that replace the hydrogen atoms of the phenolic hydroxyl groups of the polyhydric phenol compound (I) should include at least one group selected from the group consisting of the acid-dissociable, dissolution-inhibiting groups (II) and the acid-dissociable, dissolution-inhibiting groups (III). In terms of maximizing the effects of the present invention, the acid-dissociable, dissolution-inhibiting groups (II) are preferred.

Furthermore, in the compound (A1), in addition to the one or more acid-dissociable, dissolution-inhibiting groups selected from (II) and (III), a portion of the hydrogen atoms of the phenolic hydroxyl groups may also be substituted with another acid-dissociable, dissolution-inhibiting group (IV), provided such substitution does not impair the effects of the present invention. There are no particular restrictions on this other acid-dissociable, dissolution-inhibiting group (IV), which may be selected appropriately from those groups proposed for use within the hydroxystyrene-based resins and (meth)acrylic acid-based resins and the like used in chemically amplified positive resist compositions designed for use with KrF excimer lasers or ArF excimer lasers.

Specific examples include tertiary alkyl groups, tertiary alkyloxycarbonyl groups, and cyclic ether groups.

Specific examples of suitable tertiary alkyl groups include chain-like tertiary alkyl groups such as a tert-butyl group or tert-amyl group, and tertiary alkyl groups that contain an aliphatic cyclic group, such as a 2-methyl-2-adamantyl group or 2-ethyl-2-adamantyl group. In this description and in the claims, the term "aliphatic" is a relative concept used in relation to the term "aromatic", and defines a group or compound or the like that contains no aromaticity. The term "aliphatic cyclic group" describes a monocyclic group or polycyclic group that contains no aromaticity, and may be either saturated or unsaturated, but is typically saturated.

Examples of the tertiary alkyl group within tertiary alkyloxycarbonyl groups include the same groups as those described above. Specific examples of suitable tertiary alkyloxycarbonyl groups include a tert-butyloxycarbonyl group or tert-amyloxycarbonyl group.

Specific examples of suitable cyclic ether groups include a tetrahydropyranyl group or tetrahydrofuranyl group.

The compound (A1) can be produced, for example, by using a known technique to substitute either a portion of, or all of, the hydrogen atoms of the phenolic hydroxyl groups of the polyhydric phenol compound (I) with at least one of the acid-dissociable, dissolution-inhibiting groups (II) and (III), and if required with another optional acid-dissociable, dissolution-inhibiting group (IV).

In the compound (A1), the protection ratio for the phenolic hydroxyl groups, namely, the proportion of phenolic hydroxyl groups in which the hydrogen atom has been substituted with an acid-dissociable, dissolution-inhibiting group (hereafter, also referred to as "phenolic hydroxyl groups that have been protected") relative to the combined total of phenolic hydroxyl groups that have been protected with acid-dissociable, dissolution-inhibiting groups and unprotected phenolic hydroxyl groups, can be determined appropriately based on factors such as the structure of the polyhydric phenol compound (I), the number of phenolic hydroxyl groups, and the various lithography properties desired when the compound is used within a resist composition. For example, from the viewpoints of resolution and the roughness reduction effect, the protection ratio is preferably within a range from 5 to 50 mol %, even more preferably from 7 to 45 mol %, even more preferably from 10 to 40 mol %, and is most preferably from 10 to 30 mol %.

<<Positive Resist Composition>>

A positive resist composition of the present invention includes a base material component (A) that contains acid-dissociable, dissolution-inhibiting groups and exhibits increased alkali solubility under the action of acid (hereafter also referred to as the component (A)), and an acid generator component (B) that generates acid upon exposure (hereafter also referred to as the component (B)).

In the component (A), the action of the acid generated from the component (B) upon exposure causes the acid-dissociable, dissolution-inhibiting groups to dissociate, causing the entire component (A) to change from an alkali-insoluble state to an alkali-soluble state. As a result, when a resist film formed from the resist composition is selectively exposed during the formation of a resist pattern, or alternatively is exposed and then subjected to post exposure baking, the exposed portions of the resist shift to an alkali-soluble state, whereas the unexposed portions remain insoluble in alkali, meaning alkali developing can then be used to form a positive resist pattern.

In the positive resist composition of the present invention, the component (A) must contain an aforementioned compound (A1) of the present invention.

The compound (A1) may use either a single compound, or a combination of two or more different compounds.

In those cases where the compound (A1) contains two or more compounds, for example, contains a plurality of compounds for which the structure of the polyhydric phenol compound (I) is the same, but in which the number of phenolic hydroxyl groups protected with the one or more acid-dissociable, dissolution-inhibiting groups (II) and (III), and if required with another optional acid-dissociable, dissolution-inhibiting group (IV) (that is, the protection number), is different for each compound, materials in which the protection numbers for the plurality of compounds are close in value produce superior effects for the present invention, and are consequently preferred.

The proportion of each of the plurality of different compounds within the compound (A1) can be measured using a technique such as reverse-phase chromatography.

Furthermore, the protection number within each of the plurality of different compounds can be adjusted by suitable alteration of the conditions employed when the phenolic hydroxyl groups of the polyhydric phenol compound (I) are protected with the acid-dissociable, dissolution-inhibiting groups.

The component (A) may also include any of the conventional resin components that have been proposed as base material components for chemically amplified resist layers, provided the inclusion of these components does not impair the effects of the present invention.

Examples of these resin components include any of the materials proposed as base resins for conventional chemically amplified positive resist compositions for use with a KrF excimer laser or positive resist compositions for use with an ArF excimer laser, and these can be selected in accordance with the nature of the exposure light source used during resist pattern formation.

The proportion of the compound (A1) within the component (A) is preferably greater than 40% by weight, even more preferably greater than 50% by weight, even more preferably greater than 80% by weight, and is most preferably 100% by weight.

The proportion of the compound (A1) within the component (A) can be measured using a technique such as reverse-phase chromatography.

The component (A) may also include an unprotected form in which none of the phenolic hydroxyl groups within the polyhydric phenol compound (I) are protected with acid-dissociable, dissolution-inhibiting groups, namely, the polyhydric phenol compound (I) itself.

In the component (A), the proportion of the polyhydric phenol compound (I) is preferably kept as low as possible, and is preferably no higher than 60% by weight, even more preferably no higher than 50% by weight, even more preferably 10% by weight or less, and is most preferably 0% by weight. Provided the quantity of the polyhydric phenol compound (I) is no higher than 60% by weight, the effects of the present invention can be further enhanced.

The proportion of the polyhydric phenol compound (I) within the component (A) can be adjusted, for example, by using gel permeation chromatography (GPC) to remove the polyhydric phenol compound (I).

The proportion of the polyhydric phenol compound (I) within the component (A) can be measured using a technique such as reverse-phase chromatography.

The protection ratio for the phenolic hydroxyl groups within the component (A), namely, the proportion of phenolic hydroxyl groups that have been protected with acid-dissociable, dissolution-inhibiting groups relative to the combined total of phenolic hydroxyl groups that have been protected with acid-dissociable, dissolution-inhibiting groups and unprotected phenolic hydroxyl groups, can be determined appropriately based on factors such as the structure of the polyhydric phenol compound (I), the number of phenolic hydroxyl groups, and the various lithography properties desired when the compound is used within a resist composition. For example, from the viewpoints of resolution and the roughness reduction effect, the protection ratio is preferably within a range from 5 to 50 mol %, even more preferably from 7 to 45 mol %, even more preferably from 10 to 40 mol %, and is most preferably from 10 to 30 mol %.

The quantity of the component (A) within the positive resist composition of the present invention may be adjusted in accordance with the film thickness of the resist to be formed.

There are no particular restrictions on the component (B), which can use any of the acid generators proposed for use within conventional chemically amplified resists. Examples of these acid generators are numerous, and include onium salt-based acid generators such as iodonium salts and sulfonium salts, oxime sulfonate-based acid generators, diazomethane-based acid generators such as bisalkyl or bisaryl sulfonyl diazomethanes and poly(bis-sulfonyl)diazomethanes, nitrobenzyl sulfonate-based acid generators, iminosulfonate-based acid generators, and disulfone-based acid generators.

Examples of suitable onium salt-based acid generators include compounds represented by general formulas (b-1) and (b-2) shown below.

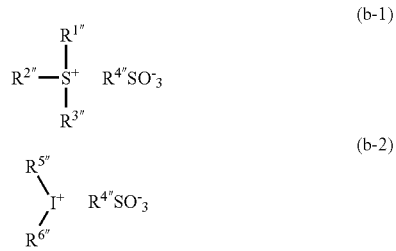

[wherein, $R^{1''}$ to $R^{3'''}$, and $R^{5''}$ to $R^{6''}$ each represent, independently, an aryl group or alkyl group; and $R^{4''}$ represents a straight-chain, branched or cyclic alkyl group or fluoroalkyl group; provided that at least one of $R^{1''}$ to $R^{3''}$ represents an aryl group, and at least one of $R^{5''}$ to $R^{6''}$ represents an aryl group]

In the formula (b-1), $R^{1''}$ to $R^{3''}$ each represent, independently, an aryl group or alkyl group. Of the groups $R^{1''}$ to $R^{3''}$, at least one group represents an aryl group. Compounds in which at least two of $R^{1''}$ to $R^{3''}$ represent aryl groups are preferred, and compounds in which all of $R^{1''}$ to $R^{3''}$ are aryl groups are the most preferred.

There are no particular restrictions on the aryl groups of $R^{1''}$ to $R^{3''}$, and suitable examples include aryl groups of 6 to 20 carbon atoms, in which either a portion of, or all of, the hydrogen atoms of these aryl groups may be either substituted, or not substituted, with alkyl groups, alkoxy groups, or halogen atoms and the like. In terms of enabling low-cost synthesis, aryl groups of 6 to 10 carbon atoms are preferred. Specific examples of suitable groups include a phenyl group and a naphthyl group.

Alkyl groups that may be used for substitution of the hydrogen atoms of the above aryl groups are preferably alkyl groups of 1 to 5 carbon atoms, and a methyl group, ethyl group, propyl group, n-butyl group or tert-butyl group are the most desirable.

Alkoxy groups that may be used for substitution of the hydrogen atoms of the above aryl groups are preferably alkoxy groups of 1 to 5 carbon atoms, and a methoxy group or ethoxy group are the most desirable. Halogen atoms that may be used for substitution of the hydrogen atoms of the above aryl groups are preferably fluorine atoms.

There are no particular restrictions on the alkyl groups of $R^{1''}$ to $R^{3''}$, and suitable examples include straight-chain, branched, or cyclic alkyl groups of 1 to 10 carbon atoms. From the viewpoint of achieving excellent resolution, alkyl groups of 1 to 5 carbon atoms are preferred. Specific examples include a methyl group, ethyl group, n-propyl group, isopropyl group, n-butyl group, isobutyl group, n-pentyl group, cyclopentyl group, hexyl group, cyclohexyl group, nonyl group, and decanyl group, although in terms of achieving superior resolution and enabling low-cost synthesis, a methyl group is the most desirable.

Of the above possibilities, compounds in which $R^{1''}$ to $R^{3''}$ are all phenyl groups are the most preferred.

The group $R^{4''}$ represents a straight-chain, branched or cyclic alkyl group or fluoroalkyl group. As the straight-chain or branched alkyl group, groups of 1 to 10 carbon atoms are preferred, groups of 1 to 8 carbon atoms are even more preferred, and groups of 1 to 4 carbon atoms are the most desirable.

Suitable cyclic alkyl groups include the same groups as those listed above in relation to the group $R^{1''}$, and cyclic groups of 4 to 15 carbon atoms are preferred, groups of 4 to 10 carbon atoms are even more preferred, and groups of 6 to 10 carbon atoms are the most desirable.

As the above fluoroalkyl group, groups of 1 to 10 carbon atoms are preferred, groups of 1 to 8 carbon atoms are even more preferred, and groups of 1 to 4 carbon atoms are the most desirable. Furthermore, the fluorination ratio of the fluoroalkyl group (namely, the fluorine atom proportion within the alkyl group) is preferably within a range from 10 to 100%, and even more preferably from 50 to 100%, and groups in which all of the hydrogen atoms have been substituted with fluorine atoms yield the strongest acids, and are consequently the most desirable.

The group $R^{4''}$ is most preferably a straight-chain or cyclic alkyl group, or a fluoroalkyl group.

In the formula (b-2), $R^{5''}$ to $R^{6''}$ each represent, independently, an aryl group or alkyl group. At least one of $R^{5''}$ to $R^{6''}$ represents an aryl group. Compounds in which all of $R^{5''}$ to $R^{6''}$ are aryl groups are preferred.

Suitable examples of the aryl groups of the groups $R^{5''}$ to $R^{6''}$ include the same aryl groups as those described above for the groups $R^{1''}$ to $R^{3''}$.

Suitable examples of the alkyl groups of the groups $R^{5''}$ to $R^{6''}$ include the same alkyl groups as those described above for the groups $R^{1''}$ to $R^{31}$.

Of the above possibilities, compounds in which $R^{5''}$ to $R^{6''}$ are all phenyl groups are the most preferred.

Suitable examples of the group $R^{4''}$ in the formula (b-2) include the same groups as those described for the group $R^{4''}$ in the aforementioned formula (b-1).

Specific examples of suitable onium salt-based acid generators include diphenyliodonium trifluoromethanesulfonate or nonafluorobutanesulfonate, bis(4-tert-butylphenyl)iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl)sulfonium trifluoromethanesulfonate, heptafluoropropanesulfonate or nonafluorobutanesulfonate, dimethyl(4-hydroxynaphthyl)sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, 38diphenylmonomethylsulfonium trifluoromethanesulfonate, heptafluoropropanesulfonate or nonafluorobutanesulfonate, (4-methylphenyl)diphenylsulfonium trifluoromethanesulfonate, heptafluoropropanesulfonate or nonafluorobutanesulfonate, (4-methoxyphenyl)diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, and diphenyl(1-(4-methoxy)naphthyl)sulfonium trifluoromethanesulfonate, heptafluoropropanesulfonate or nonafluorobutanesulfonate. Furthermore, onium salts in which the anion portion of the above onium salts have been substituted with methanesulfonate, n-propanesulfonate, n-butanesulfonate, or n-octanesulfonate can also be used.

Furthermore, compounds in which the anion portion within the above general formulas (b-1) and (b-2) has been substituted with an anion portion represented by a general formula (b-3) or (b-4) shown below (and in which the cation portion is the same as that shown in (b-1) or (b-2)) can also be used.

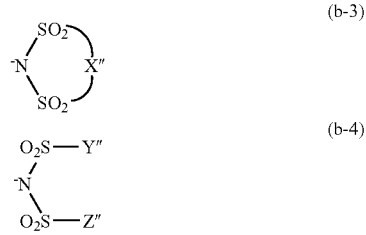

[wherein, X" represents an alkylene group of 2 to 6 carbon atoms in which at least one hydrogen atom has been substituted with a fluorine atom; Y" and Z" each represent, independently, an alkyl group of 1 to 10 carbon atoms in which at least one hydrogen atom has been substituted with a fluorine atom]

The group X" is a straight-chain or branched alkylene group in which at least one hydrogen atom has been substituted with a fluorine atom, and the number of carbon atoms within the alkylene group is typically within a range from 2 to 6, preferably from 3 to 5, and is most preferably 3.

Y" and Z" each represent, independently, a straight-chain or branched alkyl group in which at least one hydrogen atom has been substituted with a fluorine atom, and the number of carbon atoms within the alkyl group is typically within a range from 1 to 10, preferably from 1 to 7, and is most preferably from 1 to 3.

Within the above ranges for the numbers of carbon atoms, lower numbers of carbon atoms within the alkylene group X" or the alkyl groups Y" and Z" result in better solubility within the resist solvent, and are consequently preferred.

Furthermore, in the alkylene group X" or the alkyl groups Y" and Z", the larger the number of hydrogen atoms that have been substituted with fluorine atoms, the stronger the acid becomes, and the transparency relative to high energy light beams of 200 nm or less or electron beams also improves favorably. The fluorine atom proportion within the alkylene group or alkyl groups, namely the fluorination ratio, is preferably within a range from 70 to 100%, and even more preferably from 90 to 100%, and perfluoroalkylene or perfluoroalkyl groups in which all of the hydrogen atoms have been substituted with fluorine atoms are the most desirable.

In the present invention, the term "oxime sulfonate-based acid generator" describes a compound that contains at least one group represented by a general formula (B-1) shown below, and generates acid upon irradiation. These types of oxime sulfonate-based acid generators are widely used within chemically amplified resist compositions, and any of these conventional compounds can be used.

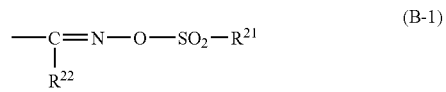

[In the formula (B-1), $R^{21}$ and $R^{22}$ each represent, independently, an organic group.]

In the present invention, the above organic groups preferably include carbon atoms, and may also include atoms other than carbon atoms (such as hydrogen atoms, oxygen atoms, nitrogen atoms, sulfur atoms, and halogen atoms (such as fluorine atoms or chlorine atoms)).

The organic group of $R^{21}$ is preferably a straight-chain, branched or cyclic alkyl group or aryl group. These alkyl groups or aryl groups may also include a substituent group. There are no particular restrictions on such substituent groups, and suitable examples include a fluorine atom or a straight-chain, branched or cyclic alkyl group of 1 to 6 carbon atoms. Here, the expression "include a substituent group" means that either a portion of, or all of, the hydrogen atoms of the alkyl group or aryl group may be substituted with substituent groups.

The alkyl group preferably contains from 1 to 20 carbon atoms, even more preferably from 1 to 10 carbon atoms, even more preferably from 1 to 8 carbon atoms, even more preferably from 1 to 6 carbon atoms, and most preferably from 1 to 4 carbon atoms. Furthermore, alkyl groups that are partially or completely halogenated (hereafter also referred to as haloalkyl groups) are preferred. A partially halogenated alkyl group is an alkyl group in which a portion of the hydrogen atoms have been substituted with halogen atoms, whereas a completely halogenated alkyl group is an alkyl group in which all of the hydrogen atoms have been substituted with halogen atoms. Examples of the halogen atoms include fluorine atoms, chlorine atoms, bromine atoms or iodine atoms, although fluorine atoms are particularly desirable. In other words, the haloalkyl group is preferably a fluoroalkyl group.

The aryl group preferably contains from 4 to 20 carbon atoms, even more preferably from 4 to 10 carbon atoms, and most preferably from 6 to 10 carbon atoms. Aryl groups that are partially or completely halogenated are preferred. A partially halogenated aryl group is an aryl group in which a portion of the hydrogen atoms have been substituted with halogen atoms, whereas a completely halogenated aryl group is an aryl group in which all of the hydrogen atoms have been substituted with halogen atoms.

As the group $R^{21}$, an alkyl group of 1 to 4 carbon atoms containing no substituent groups, or a fluoroalkyl group of 1 to 4 carbon atoms is the most desirable.

The organic group of $R^{22}$ is preferably a straight-chain, branched or cyclic alkyl group or aryl group, or a cyano group. Examples of suitable alkyl groups and aryl groups for $R^{22}$ include the same alkyl groups and aryl groups described above in relation to $R^{21}$.

As the group $R^{22}$, a cyano group, an alkyl group of 1 to 8 carbon atoms containing no substituent groups, or a fluoroalkyl group of 1 to 8 carbon atoms is the most desirable.

Particularly preferred oxime sulfonate-based acid generators include the compounds represented by the general formulas (B-2) and (B-3) shown below.

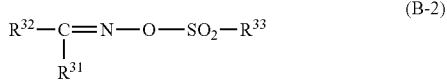

(B-2)

[In the formula (B-2), $R^{31}$ represents a cyano group, an alkyl group containing no substituent groups, or a haloalkyl group. $R^{32}$ represents an aryl group. $R^{33}$ represents an alkyl group containing no substituent groups, or a haloalkyl group.]

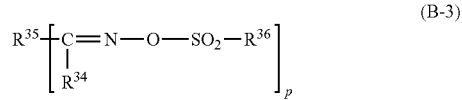

(B-3)

[In the formula (B-3), $R^{34}$ represents a cyano group, an alkyl group containing no substituent groups, or a haloalkyl group. $R^{35}$ represents a bivalent or trivalent aromatic hydrocarbon group. $R^{36}$ represents an alkyl group containing no substituent groups, or a haloalkyl group. p is either 2 or 3.]

In the above general formula (B-2), the alkyl group containing no substituent groups or haloalkyl group represented by $R^{31}$ preferably contains from 1 to 10 carbon atoms, even more preferably from 1 to 8 carbon atoms, and most preferably from 1 to 6 carbon atoms.

The group $R^{31}$ is preferably a haloalkyl group, and even more preferably a fluoroalkyl group.

In the fluoroalkyl group of $R^{31}$, at least 50% of the hydrogen atoms of the alkyl group are preferably fluorinated, and this ratio is even more preferably 70% or higher, and is most preferably 90% or higher.

The aryl group represented by $R^{32}$ is preferably a group in which one hydrogen atom has been removed from an aromatic hydrocarbon ring, such as a phenyl group, biphenyl group, fluorenyl group, naphthyl group, anthracyl (anthryl) group or phenanthryl group, or a heteroaryl group in which a portion of the carbon atoms that constitute the ring structure within the above groups have been substituted with a hetero atom such as an oxygen atom, sulfur atom or nitrogen atom. Of these possibilities, a fluorenyl group is particularly preferred.

The aryl group of $R^{32}$ may include a substituent group such as an alkyl group, haloalkyl group or alkoxy group of 1 to 10 carbon atoms. The alkyl group or haloalkyl group substituent groups preferably contain from 1 to 8 carbon atoms, and even more preferably 1 to 4 carbon atoms. Furthermore, the haloalkyl group is preferably a fluoroalkyl group.

The alkyl group containing no substituent groups or haloalkyl group represented by $R^{33}$ preferably contains from 1 to 10 carbon atoms, even more preferably from 1 to 8 carbon atoms, and most preferably from 1 to 6 carbon atoms.

The group $R^{33}$ is preferably a haloalkyl group, and even more preferably a partially or totally fluorinated alkyl group.

In the fluoroalkyl group of $R^{33}$, at least 50% of the hydrogen atoms of the alkyl group are preferably fluorinated, and groups in which 70% or more, and even more preferably 90% or more, of the hydrogen atoms are fluorinated are particularly desirable as they increase the strength of the acid that is generated. Completely fluorinated alkyl groups in which 100% of the hydrogen atom have been substituted with fluorine atoms are the most desirable.

In the above general formula (B-3), examples of the alkyl group containing no substituent groups or haloalkyl group represented by $R^{34}$ include the same alkyl groups containing no substituent groups and haloalkyl groups described above for the group $R^{31}$.

Examples of the bivalent or trivalent aromatic hydrocarbon group represented by $R^{35}$ include groups in which a further one or two hydrogen atoms respectively are removed from an aryl group of the aforementioned group $R^{32}$.

Examples of the alkyl group containing no substituent groups or haloalkyl group represented by $R^{36}$ include the same alkyl groups containing no substituent groups and haloalkyl groups described above for the group $R^{33}$.

p is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)-benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Furthermore, further examples include the compounds represented by the chemical formulas shown below.

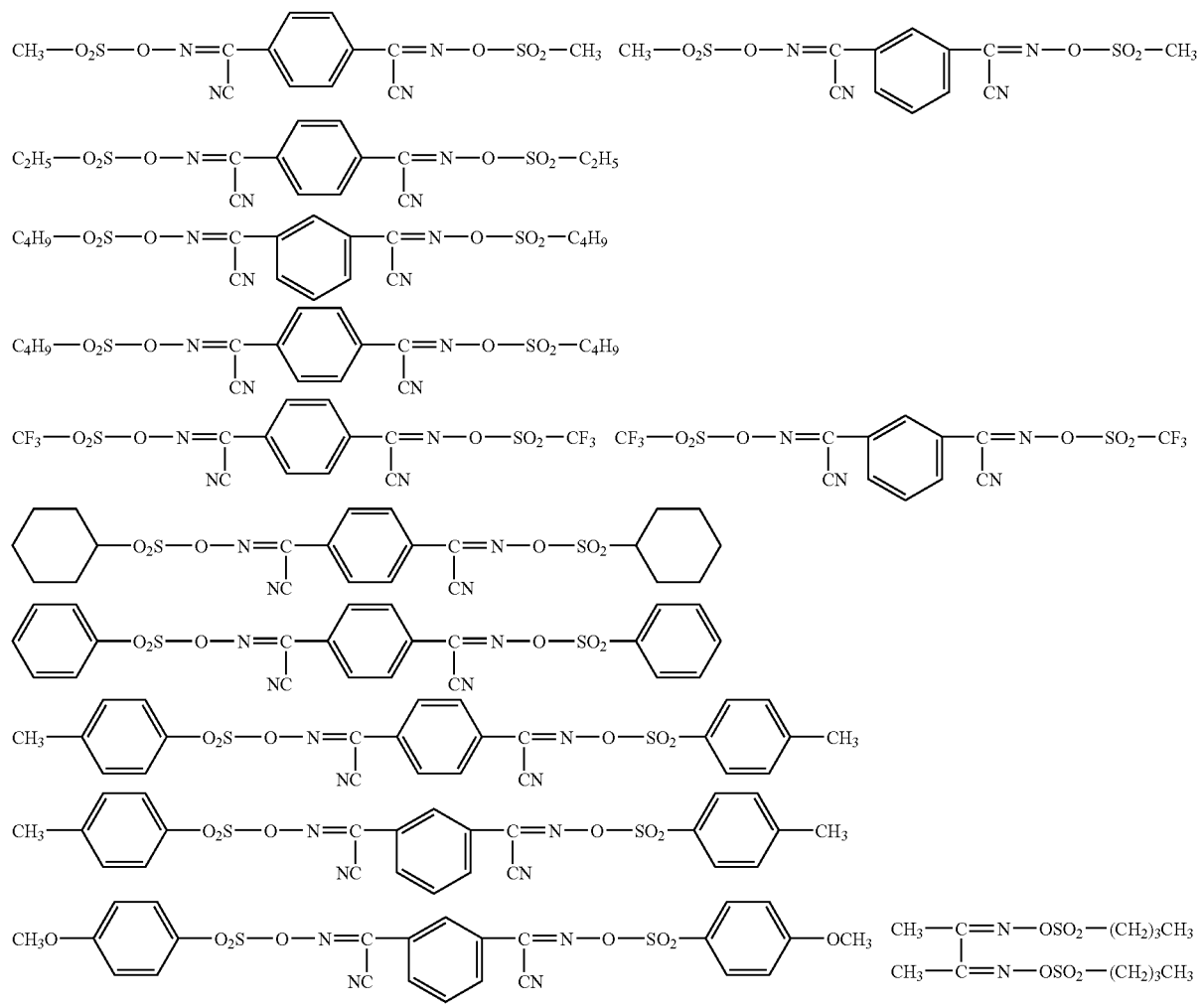
Furthermore, of the compounds represented by the aforementioned general formulas (B-2) and (B-3), examples of particularly preferred compounds include those shown below.

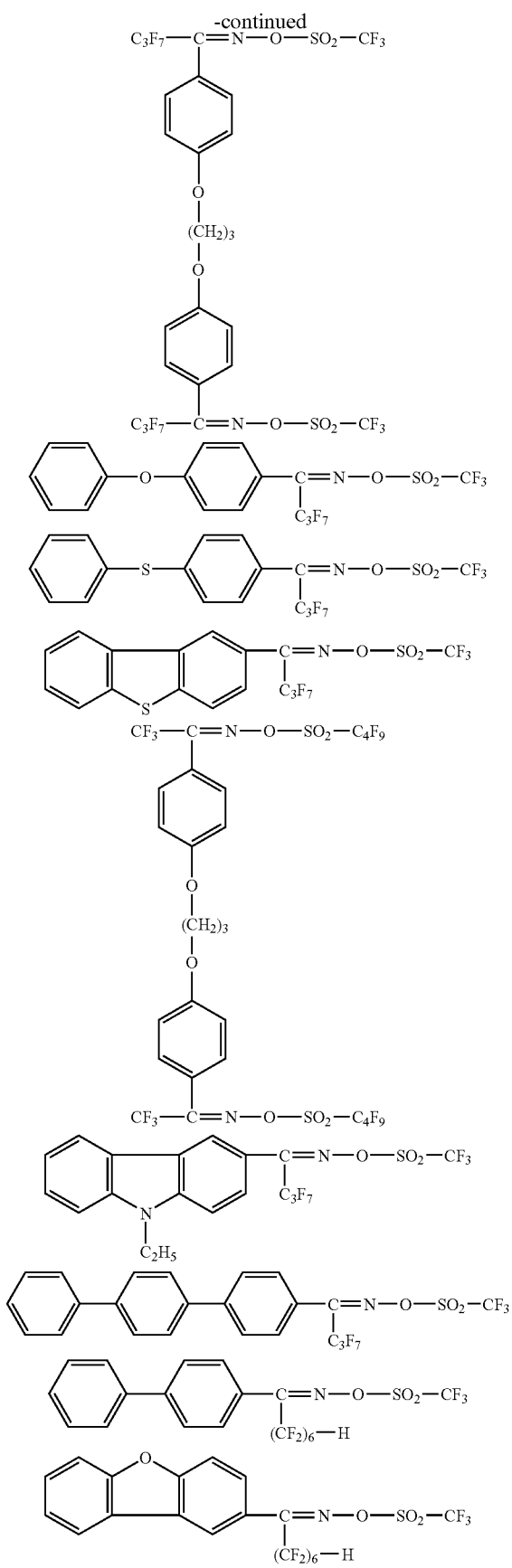
Of the above compounds, the three compounds shown below are particularly desirable.

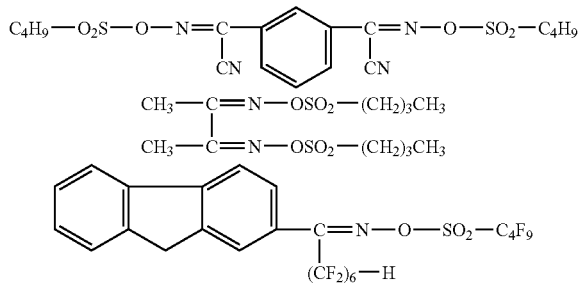

Of the various diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Furthermore, specific examples of poly(bis-sulfonyl)diazomethanes include the structures shown below, such as 1,3-bis(phenylsulfonyldiazomethylsulfonyl)propane (wherein A=3), 1,4-bis(phenylsulfonyldiazomethylsulfonyl)butane (wherein A=4), 1,6-bis(phenylsulfonyldiazomethylsulfonyl)hexane (wherein A=6), 1,10-bis(phenylsulfonyldiazomethylsulfonyl)decane (wherein A=10), 1,2-bis(cyclohexylsulfonyldiazomethylsulfonyl)ethane (wherein B=2), 1,3-bis(cyclohexylsulfonyldiazomethylsulfonyl)propane (wherein B=3), 1,6-bis(cyclohexylsulfonyldiazomethylsulfonyl)hexane (wherein B=6), and 1,10-bis(cyclohexylsulfonyldiazomethylsulfonyl)decane (wherein B=10).

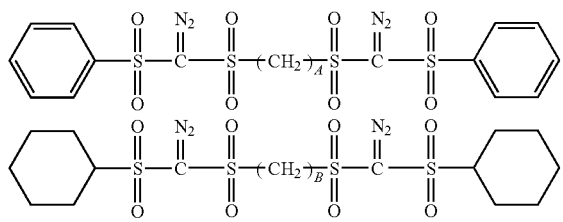

In the present invention, of the various possibilities, the component (B) is preferably an onium salt containing a fluorinated alkylsulfonate ion or alkylsulfonate ion as the anion.

As the component (B), either a single acid generator may be used alone, or a combination of two or more of these acid generators may be used.

The blend quantity of the component (B) is typically within a range from 0.5 to 30 parts by weight, and preferably from 1 to 10 parts by weight, per 100 parts by weight of the component (A). Ensuring the quantity satisfies this range enables satisfactory pattern formation to be achieved. Furthermore, a uniform solution can be obtained, and the storage stability is also favorable.

[Optional Components]

In the positive resist composition, in order to improve the resist pattern shape and the post exposure stability of the latent image formed by the pattern-wise exposure of the resist layer, a nitrogen-containing organic compound (D) (hereafter referred to as the component (D)) may be added as an optional component.

A multitude of these nitrogen-containing organic compounds have already been proposed, and any of these known compounds can be used, and suitable examples include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Of these compounds, secondary aliphatic amines and tertiary aliphatic amines are preferred, trialkylamines of 5 to 10 carbon atoms are even more preferred, and tri-n-octylamine is the most desirable.

These compounds may be used either alone, or in combinations of two or more different compounds.

The component (D) is typically used in a quantity within a range from 0.01 to 5.0 parts by weight per 100 parts by weight of the component (A).

Furthermore, in order to prevent any deterioration in sensitivity caused by the addition of the above component (D), and improve the resist pattern shape and the post exposure stability of the latent image formed by the pattern-wise exposure of the resist layer, an organic carboxylic acid, or a phosphorus oxo acid or derivative thereof (E) (hereafter referred to as the component (E)) may also be added to the positive resist composition of the present invention as another optional component. The component (D) and the component (E) can be used in combination, or either one can also be used alone.

Examples of suitable organic carboxylic acids include malonic acid, citric acid, malic acid, succinic acid, benzoic acid, and salicylic acid.

Examples of suitable phosphorus oxo acids or derivatives thereof include phosphoric acid or derivatives thereof such as esters, including phosphoric acid, di-n-butyl phosphate and diphenyl phosphate; phosphonic acid or derivatives thereof such as esters, including phosphonic acid, dimethyl phosphonate, di-n-butyl phosphonate, phenylphosphonic acid, diphenyl phosphonate, and dibenzyl phosphonate; and phosphinic acid or derivatives thereof such as esters, including phosphinic acid and phenylphosphinic acid, and of these, phosphonic acid is particularly preferred.

The component (E) is typically used in a quantity within a range from 0.01 to 5.0 parts by weight per 100 parts by weight of the component (A).

Other miscible additives can also be added to the positive resist composition of the present invention according to need, and examples include additive resins for improving the performance of the resist film, surfactants for improving the coating properties, dissolution inhibitors, plasticizers, stabilizers, colorants, halation prevention agents, and dyes and the like.

The positive resist composition of the present invention can be produced by dissolving the aforementioned component (A) and component (B), together with any of the various optional components, in an organic solvent.

The organic solvent may be any solvent capable of dissolving the various components used to generate a uniform solution, and one or more solvents selected from known materials used as the solvents for conventional chemically amplified resists can be used.

Examples of the solvent include lactones such as γ-butyrolactone, ketones such as acetone, methyl ethyl ketone, cyclohexanone, methyl isoamyl ketone and 2-heptanone, polyhydric alcohols and derivatives thereof such as ethylene glycol, ethylene glycol monoacetate, diethylene glycol, diethylene glycol monoacetate, propylene glycol, propylene glycol monoacetate, dipropylene glycol, the monomethyl ether, monoethyl ether, monopropyl ether, monobutyl ether or monophenyl ether of dipropylene glycol monoacetate, and propylene glycol monomethyl ether acetate (PGMEA), cyclic ethers such as dioxane, and esters such as methyl lactate, ethyl lactate (EL), methyl acetate, ethyl acetate, butyl acetate, methyl pyruvate, ethyl pyruvate, methyl methoxypropionate, and ethyl ethoxypropionate.

These organic solvents may be used either alone, or as a mixed solvent containing two or more different solvents.

Furthermore, mixed solvents produced by mixing propylene glycol monomethyl ether acetate (PGMEA) with a polar solvent are preferred. Although the blend ratio (weight ratio) in such mixed solvents can be set in accordance with factors such as the co-solubility of the PGMEA and the polar solvent, the ratio is preferably within a range from 1:9 to 9:1, and is even more preferably from 2:8 to 8:2.

More specifically, in those cases where EL is added as the polar solvent, the weight ratio PGMEA:EL is preferably within a range from 1:9 to 9:1, and is even more preferably from 2:8 to 8:2.

Furthermore, as the organic solvent, mixed solvents containing at least one of PGMEA and EL, together with γ-butyrolactone, are also preferred. In such cases, the weight ratio of the former and latter components in the mixed solvent is preferably within a range from 70:30 to 95:5.

There are no particular restrictions on the quantity used of the organic solvent, although the quantity should be set in accordance with the coating film thickness required, at a concentration that enables favorable application of the solution to a substrate or the like, and typically the quantity of solvent is set so that the solid fraction concentration of the resist composition falls within a range from 2 to 20% by weight, and preferably from 5 to 15% by weight.

<<Method for Forming Resist Pattern>>

A method for forming a resist pattern according to the present invention includes the steps of: forming a resist film on a substrate using the positive resist composition according to the present invention described above, conducting exposure of the resist film, and developing the resist film to form a resist pattern.

More specifically, a resist pattern can be formed, for example, using the method for forming a resist pattern described below.

Namely, the positive resist composition described above is first applied to a substrate such as a silicon wafer using a spinner or the like, and an optional prebake (PAB) is then conducted, thereby forming a resist film. Following selective exposure of the thus formed resist film, either by exposure through a mask pattern using an exposure apparatus such as an electron beam lithography apparatus or an EUV exposure apparatus, or by patterning via direct irradiation with an electron beam without using a mask pattern, PEB (post exposure baking) is conducted. Subsequently, developing is conducted using an alkali developing solution, a rinse treatment is performed to wash away the residual developing solution on the substrate and the portions of the resist composition that have been dissolved by the developing solution, and the resist is then dried, yielding a resist pattern.

These steps can be conducted using conventional techniques. The conditions during the operation are preferably set in accordance with factors such as the formulation and properties of the positive resist composition.

There are no particular restrictions on the exposure source, and an ArF excimer laser, KrF excimer laser, $F_2$ excimer laser, or other radiation such as EUV (extreme ultra violet), VUV (vacuum ultra violet), electron beam, X-ray or soft X-ray radiation can be used. The positive resist composition according to the present invention is particularly effective for use with an electron beam or EUV radiation, and an electron beam is particularly desirable.

In some cases, the method may include a post bake step following the above alkali developing step, and an organic or inorganic anti-reflective film may also be provided between the substrate and the resist film.

As described above, according to the compound (A1) of the present invention, a positive resist composition containing the compound (A1), and a method for forming a resist pattern that uses the positive resist composition, a resist pattern with a high level of resolution can be formed. Furthermore, the level of roughness on the upper and side wall surfaces of the pattern can also be reduced.

It is thought that the reason for the improvement in resolution is that because the compound (A1) has a structure in which the basic skeleton is based on the polyhydric phenol compound (I), and the phenolic hydroxyl groups of the phenol compound are protected with at least one group selected from the acid-dissociable, dissolution-inhibiting groups (II) and (III), a resist film obtained using a positive resist composition that contains this compound (A1) will exhibit a more uniform dissolution behavior relative to the developing solution.

In other words, with conventional resists that use a polymer as the base material component, during the spin coating process used for forming the resist film, those molecules with a higher level of hydrophilicity and those molecules with a higher level of hydrophobicity tend to accumulate in a partially localized manner, meaning fluctuations tend to develop in the distribution within the resist film of the various components such as the component (B) and the like. Furthermore, variations also develop in the degree of dissociation of the acid-dissociable, dissolution-inhibiting groups within the polymer compound. It is thought that, as a result, roughness has tended to increase and the resolution has tended to deteriorate as a result of factors such as a lack of uniformity in the rate at which the acid-dissociable, dissolution-inhibiting groups undergo dissociation (the deprotection reaction) under the action of the generated acid at the interface between the exposed portions and the unexposed portions, fluctuations in the alkali solubility of the various base material component molecules following the deprotection reaction, and fluctuations in the solubility rate of the resist film.

In contrast, in the present invention, it is thought that because the compound (A1) has the structure described above, the properties (such as the hydrophilicity, hydrophobicity and crystallinity) of a resist film obtained using a positive resist composition that contains the compound (A1) are more uniform, and moreover, it is also thought that because the acid-dissociable, dissolution-inhibiting groups (II) or (III), or the combination of (II) and (III) also dissociate more readily, the dissociation of the acid-dissociable, dissolution-inhibiting groups at the time of exposure also occurs in a more uniform manner. In other words, it is surmised that because a uniform film can be formed, and the acid-dissociable, dissolution-inhibiting groups also dissociate in a uniform manner, roughness can be reduced and a high level of resolution can be achieved. Furthermore, a resist pattern of favorable shape can also be formed.

EXAMPLES

As follows is a description of examples of the present invention, although the scope of the present invention is in no way limited by these examples.

Production Example 1

Synthesis of a Precursor (I-1a) to the Polyhydric Phenol Compound (I-1)

Under an atmosphere of nitrogen, 244.0 g (2.0 mol) of salicylaldehyde was weighed into a four-neck flask with a capacity of 1 liter fitted with a reflux condenser, a thermometer and a stirrer, and 114.0 g (1.0 mol) of trifluoroacetic acid was then added dropwise to the flask over a period of 30 minutes and stirred at room temperature. 98.4 g (0.2 mol) of a powdered form of 6-cyclohexyl-4-{[3-cyclohexyl-4-hydroxy-5-(hydroxymethyl)phenyl]cyclohexyl}-2-(hydroxymethyl)phenol was then added to the mixed solution intermittently at 30° C. over a 6 hour period, and the resulting mixture was then stirred for 18 hours. Following the addition of 210.0 g of toluene to the reaction mixture, the reaction system was neutralized by adding an aqueous solution of sodium hydroxide with a concentration of 16% by weight. The neutralized reaction mixture was heated to 70° C., the phases were separated, and the 377.6 g aqueous phase (layer) was removed.

150.0 g of ion-exchanged water was added to the residue left in the flask, water washing was conducted at 70° C., and the water phase was then separated and removed. This operation was repeated three times, the resulting residue left within the flask was concentrated under reduced pressure at 160° C. and 2.7 kPa, and following the addition of 140.0 g of toluene to the residue at 110° C., 280.0 g of cyclohexane was added at 80° C. and the product was crystallized. The resulting crystals were isolated by filtration, yielding 108.9 g of the targeted product (the precursor (I-1a) represented by a chemical formula (I-1a) shown below). The yield was 77.8%.

The IUPAC name for the precursor (I-1a) is (5-{[5-({3-[(3-carbonyl-4-hydroxyphenyl)methyl]-5-cyclohexyl-4-hydroxyphenyl}cyclohexyl)-3-cyclohexyl-2-hydroxyphenyl]methyl}-2-hydroxyphenyl)formaldehyde.

Measurement of the molecular weight of the thus obtained precursor (I-1a) using a liquid chromatography-mass spectrometry method (LC-MS) confirmed that the targeted product had been obtained.

Furthermore, the results of proton nuclear magnetic resonance spectral analysis (400 MHz, solvent: DMSO-$d_6$ (dimethylsulfoxide-$d_6$ (a deuterated solvent))) of the precursor (I-1a) are shown in the chemical formula below and in Table 1.

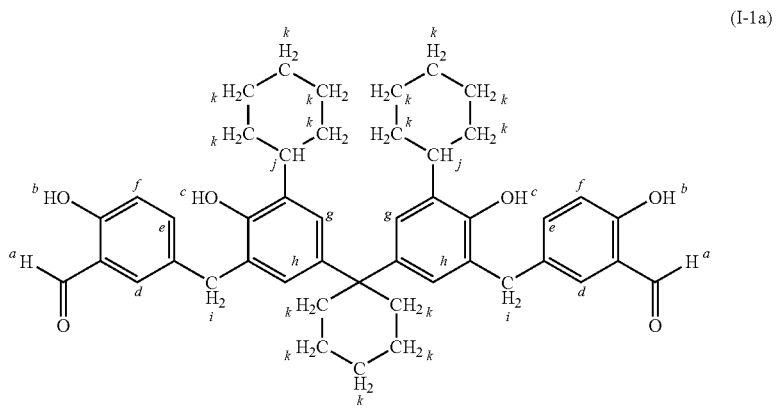

TABLE 1

| Shift value (ppm) | Assignment | Signal type | Number of protons |
|---|---|---|---|
| 10.49 | a | s | 2 |
| 10.19 | b | s | 2 |
| 7.98 | c | s | 2 |
| 7.49 | d | d | 2 |
| 7.27 | e | dd | 2 |
| 6.85 | f | d | 2 |

TABLE 1-continued

| Shift value (ppm) | Assignment | Signal type | Number of protons |
|---|---|---|---|
| 6.81 | g | s | 2 |
| 6.77 | h | s | 2 |
| 3.80 | i | s | 2 |
| 2.88 to 2.82 | j | m | 2 |
| 2.09 to 1.14 | k | m | 30 |

Production Example 2

Synthesis of Polyhydric Phenol Compound (I-1)

33.6 g (0.28 mol) of 2,5-xylenol, 50.4 g of methanol and 10.1 g of an aqueous solution of hydrochloric acid with a concentration of 35% by weight were weighed into a four-neck flask with a capacity of 500 ml, and 38.5 g (0.06 mol) of the precursor (I-1a) obtained in the above production example 1 was then added at 40° C. over a period of 2 hours. Subsequently, the reaction was continued under stirring at 40° C. for 46 hours.

Subsequently, the reaction system was neutralized using 33.8 g of an aqueous solution of sodium hydroxide with a concentration of 16% by weight, and the temperature was then raised to 60° C., 102.4 g of methyl isobutyl ketone was added to dissolve the product, and the phases were separated. Subsequently, a concentration was conducted at atmospheric pressure to remove 180 g by distillation, 126.8 g of toluene and 31.7 g of cyclohexane were added, and crystals were precipitated from the system. These crystals were cooled to 25° C. and then collected by filtration, thus yielding crude crystals These crude crystals, 100 g of propyl acetate and 60 g of water were combined in a four-neck flask with a capacity of 500 ml, and following dissolution by heating to 70° C., the system was allowed to stand for 10 minutes, the water layer was removed, a further 60 g of water was added, and the same operation of washing with water followed by separation of the water layer was conducted. Subsequently, a concentration was conducted at atmospheric pressure to remove 94 g by distillation, and 130 g of toluene and 50 g of cyclohexane were added. The resulting mixture was cooled to 25° C., and the precipitate was filtered off and dried, yielding 43.4 g of a light yellow powder of the target product (the polyhydric phenol compound (I-1)). The yield relative to the precursor (I-1a) was 68.5%.

The IUPAC name for the polyhydric phenol compound (I-1) is 4-({5-[(5-{[3-({3-[bis(4-hydroxy-2,5-dimethylphenyl)methyl]-4-hydroxyphenyl}methyl)-5-cyclohexyl-4-hydroxyphenyl]cyclohexyl]-3-cyclohexyl-2-hydroxyphenyl)methyl]-2-hydroxyphenyl} (4-hydroxy-2,5-dimethylphenyl)methyl)-2,5-dimethylphenol.

Measurement of the molecular weight of the thus obtained polyhydric phenol compound (I-1) using a liquid chromatography-mass spectrometry method (LC-MS) confirmed that the targeted product had been obtained.

The results of proton nuclear magnetic resonance spectral analysis (400 MHz, solvent: DMSO-$d_6$ (dimethylsulfoxide-$d_6$ (a deuterated solvent))) are shown in the chemical formula below and in Table 2.

Furthermore, the purity of the thus obtained polyhydric phenol compound (I-1) as measured by high performance liquid chromatography (HPLC) was 97.4%, and the melting point (DSC [differential scanning calorimeter], measured at peak top) was 178.5° C.

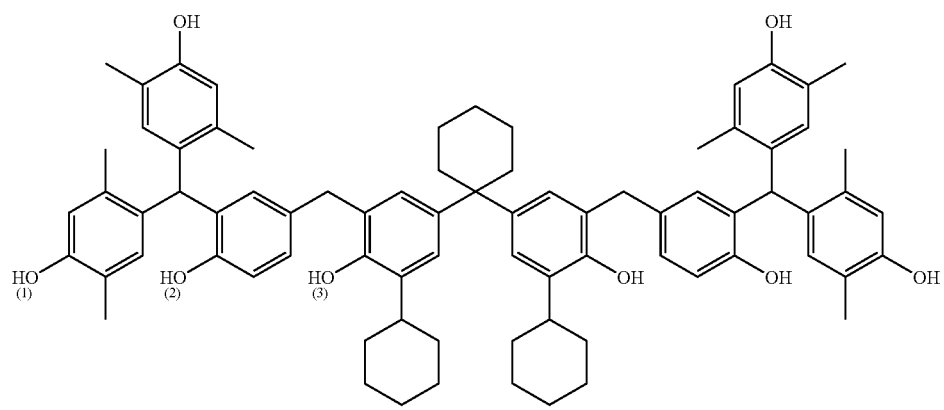

(I-1)

TABLE 2

| Shift value (ppm) | Number of protons | Signal type | Assignment |
|---|---|---|---|
| 1.18 to 1.72 | 26 | m | —$CH_2$ (cyclohexyl) |
| 1.93 to 1.96 | 24 + 4 | m | —$CH_3$ + —$CH_2$ (cyclohexyl) |
| 2.85 | 2 | t | —CH (cyclohexyl) |
| 3.63 | 4 | s | —$CH_2$ |
| 5.65 | 2 | s | —CH |
| 6.54 to 6.74 | 18 | m | Ph-H |
| 7.76 | 2 | s | —OH (Ph-OH): (3) |
| 8.84 | 4 | s | —OH (Ph-OH): (1) |
| 8.96 | 2 | s | —OH (Ph-OH): (2) |

Production Example 3

Synthesis of Compound (A1-1)

The reaction equation is shown below.

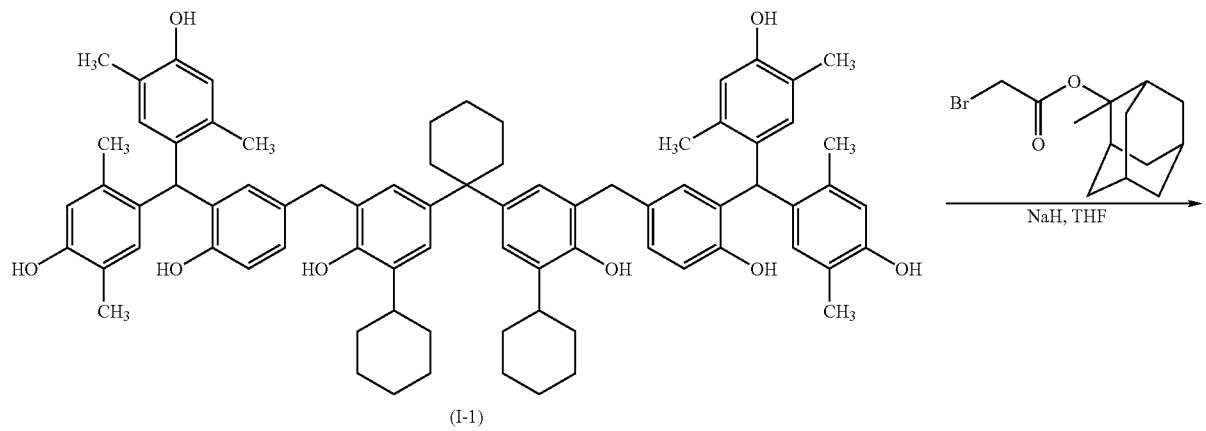

(I-1)

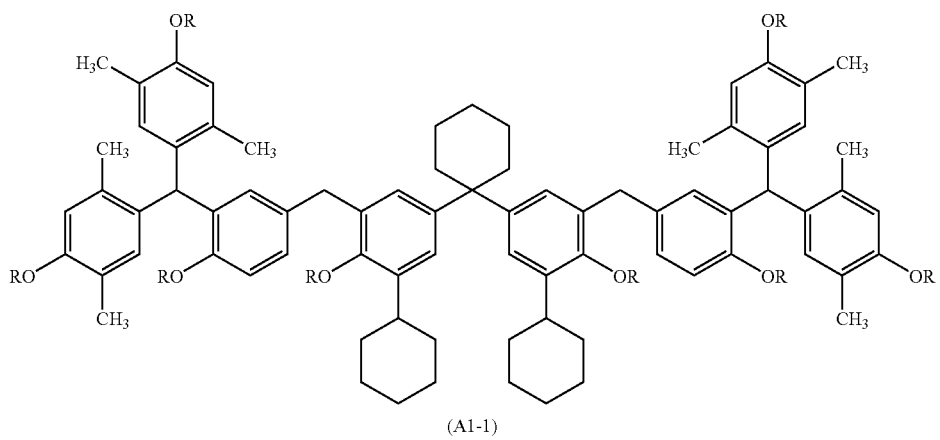

(A1-1)

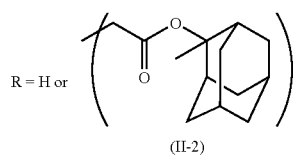

R = H or (II-2)

5 g of the polyhydric phenol compound (I-1) obtained in the above production example 2 was dissolved in 20 g of tetrahydrofuran (THF), 0.4 g of 60% by weight sodium hydride (a commercial product) was added at 0° C., and the mixture was stirred for 10 minutes. Subsequently, 2.6 g of 2-methyl-2-adamantl bromoacetate was added, and the resulting mixture was stirred at room temperature for a further 10 hours. Following completion of the reaction, the product was extracted using water/ethyl acetate, and the resulting ethyl acetate solution was dried over sodium sulfate and then concentrated under reduced pressure, yielding 5.3 g of a compound (A1-1). The compound (A1-1) is a compound in which a portion of the phenolic hydroxyl groups of the polyhydric phenol compound (I-1) have been substituted with acid-dissociable, dissolution-inhibiting groups represented by the formula (II-2), and the phenolic hydroxyl group protection ratio (calculated by $^1$H-NMR) was 25.9 mol %.

$^1$H-NMR (DMSO-$d_6$, internal standard: tetramethylsilane) δ=8.73 to 8.99 (m, 4.06H), 7.67 to 7.79 (m, 1.87H), 6.28 to 6.87 (m, 18H), 5.60 to 5.91 (m, 2H), 4.44 to 4.70 (m, 4.14H), 3.54 to 3.75 (m, 4H), 2.76 to 2.91 (m, 2H), 1.94 (s, 12H), 1.89 (s, 12H), 1.15 to 2.25 (m, 65.2H)

Production Example 4

Synthesis of Compound (A1-2)

The reaction equation is shown below.

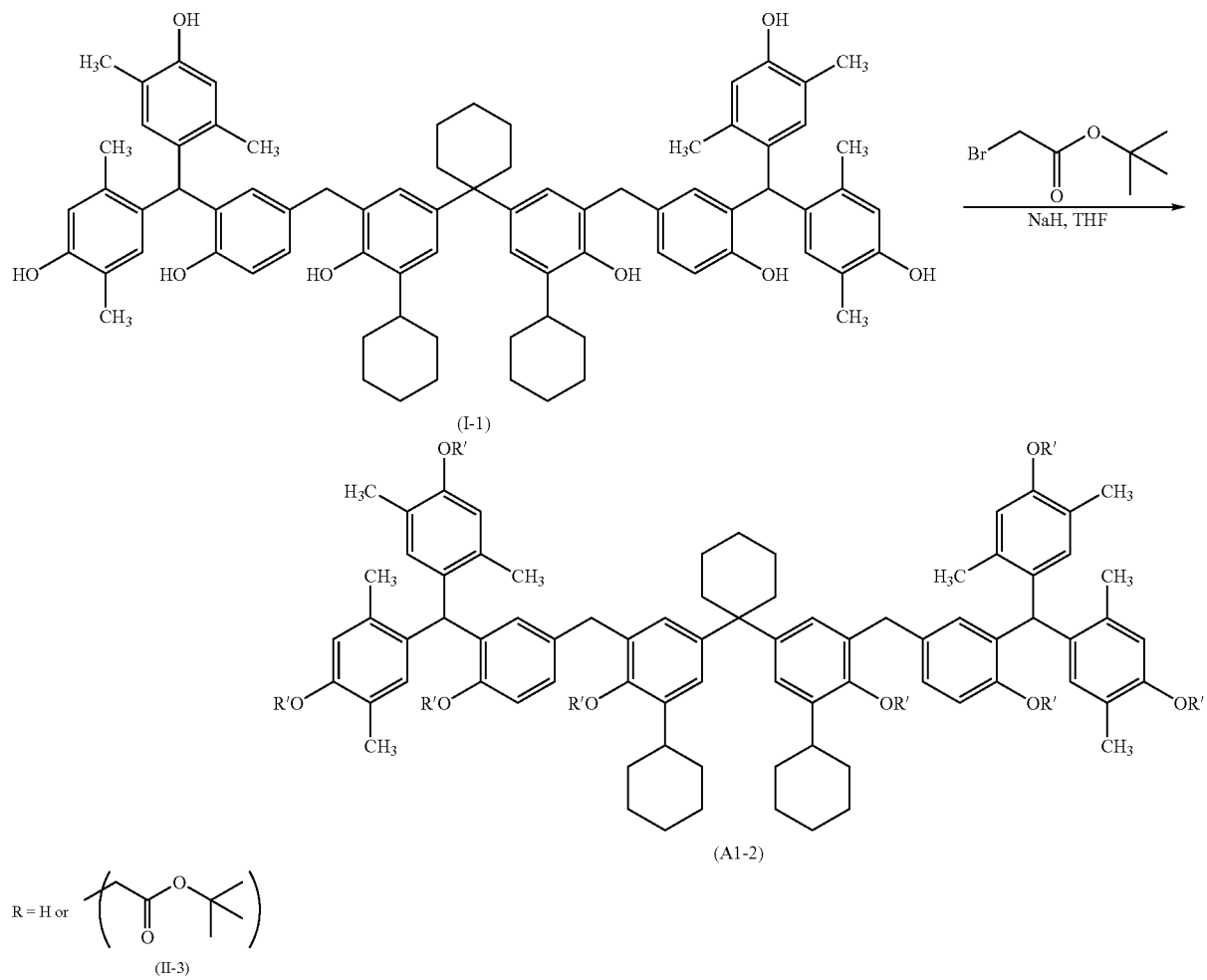

With the exception of replacing the 2.6 g of 2-methyl-2-adamantl bromoacetate with 1.7 g of tert-butyl bromoacetate, reaction was conducted using the same procedure as the production example 3, and yielded 5.2 g of a compound (A1-2). The compound (A1-2) is a compound in which a portion of the phenolic hydroxyl groups of the polyhydric phenol compound (I-1) have been substituted with acid-dissociable, dissolution-inhibiting groups represented by the formula (II-3), and the phenolic hydroxyl group protection ratio (calculated by $^1$H-NMR) was 15.6 mol %.

$^1$H-NMR (DMSO-$d_6$, internal standard: tetramethylsilane) δ=8.72 to 9.01 (m, 4.87H), 7.65 to 7.78 (m, 1.88H), 6.23 to 6.88 (m, 18H), 5.59 to 5.90 (m, 2H), 4.37 to 4.65 (m, 2.50H), 3.55 to 3.75 (m, 4H), 2.79 to 2.90 (m, 2H), 1.95 (s, 121), 1.90 (s, 12H), 1.15 to 2.10 (m, 30H)

Examples 1 and 2

Comparative Example 1 and 2

The components shown in Table 3 were mixed together and dissolved, yielding a series of positive resist composition solutions.

In Table 3, the numerical values within the brackets [ ] represent blend quantities (parts by weight).

TABLE 3

|  | Component (A) | Component (B) | Component (D) | Organic solvent |
|---|---|---|---|---|
| Example 1 | Compound (A1-1) [100] | PAG 1 [10] | Amine 1 [1.0] | Solvent 1 [1550] |
| Example 2 | Compound (A1-2) [100] | PAG 1 [10] | Amine 1 [1.0] | Solvent 1 [1550] |
| Comparative example 1 | Resin (1) [100] | PAG 1 [10] | Amine 1 [1.0] | Solvent 1 [1550] |
| Comparative example 2 | Resin (2) [100] | PAG 1 [10] | Amine 1 [1.0] | Solvent 1 [1550] |

Resin (1) is a resin in which 16.4 mol % of the hydroxyl groups within a polyhydroxystyrene (weight average molecular weight (Mw)=8,000, Mw/Mn=2.65) have been substituted with acid-dissociable, dissolution-inhibiting groups represented by the above formula (II-2).

Resin (2) is a resin in which 19.1 mol % of the hydroxyl groups within a polyhydroxystyrene (weight average molecular weight (Mw)=8,000, Mw/Mn=2.65) have been substituted with acid-dissociable, dissolution-inhibiting groups represented by the above formula (II-3).

PAG 1 is triphenylsulfonium nonafluorobutanesulfonate.

Amine 1 is tri-n-octylamine.

Solvent 1 is a mixed solvent in which PGMEA/EL=6/4 (weight ratio).

Subsequently, using the prepared positive resist composition solutions, the evaluations described below were conducted. The results of the evaluations are shown in Table 4.

<Sensitivity>

Each positive resist composition solution was applied uniformly, using a spinner, to the surface of an 8-inch silicon substrate that had been treated with hexamethyldisilazane, and was then subjected to a bake treatment (PAB) at 110° C. for 90 seconds, thus forming a resist film (film thickness: 150 nm).

This resist film was then subjected to direct patterning (exposure) with an electron beam lithography apparatus HL-800D (VSB) (manufactured by Hitachi, Ltd.) at an accelerating voltage of 70 kV, and was subsequently subjected to a bake treatment (PEB) at 110° C. for 90 seconds, developed for 60 seconds in a 2.38% by weight aqueous solution (at 23° C.) of tetramethylanumonium hydroxide (TMAH), and then rinsed in pure water for 30 seconds, thus forming a line and space (L/S) pattern.

The exposure dose Eop (μC/cm$^2$) at which a 100 nm L/S pattern was formed in a 1:1 ratio was determined.

<Resolution>

The critical resolution (nm) at the above Eop value was determined using a scanning electron microscope S-9220 (manufactured by Hitachi, Ltd.).

<Resist Pattern Shape>

The shape of a 1:1 100 nm L/S pattern was inspected using a scanning electron microscope S-9220 (manufactured by Hitachi, Ltd.).

TABLE 4

| | Sensitivity | Resolution |
| --- | --- | --- |
| Example 1 | 38 μC/cm$^2$ | 80 nm |
| Example 2 | 30 μC/cm$^2$ | 70 nm |
| Comparative example 1 | 30 μC/cm$^2$ | 90 nm |
| Comparative example 2 | 26 μC/cm$^2$ | 90 nm |

As is evident from the above results, comparison of those compositions with the same acid-dissociable, dissolution-inhibiting groups, namely the example 1 and the comparative example 1, and the example 2 and the comparative example 2 respectively, showed that the examples 1 and 2 exhibited improved resolution. Furthermore, the resist pattern shapes for the examples 1 and 2 also exhibited superior rectangular formability when compared with those of the comparative examples 1 and 2.

INDUSTRIAL APPLICABILITY

The present invention provides a positive resist composition and a method for forming a resist pattern that are capable of forming a very fine pattern with a high level of resolution, and also provides a compound that is ideal for use within the positive resist composition.

The invention claimed is:

1. A positive resist composition, comprising:
   a base material component (A) that contains an acid-dissociable, dissolution-inhibiting group and exhibits increased alkali solubility under action of acid; and
   an acid generator component (B) that generates acid upon exposure, wherein
   said base material component (A) comprises a compound (A1), in which either a portion of, or all of, hydrogen atoms of phenolic hydroxyl groups within a polyhydric phenol compound with a molecular weight of 300 to 2,500 represented by a general formula (I) shown below have been substituted with at least one group selected from the group consisting of acid-dissociable, dissolution-inhibiting groups represented by a general formula (II) shown below and acid-dissociable, dissolution-inhibiting groups represented by a general formula (III) shown below:

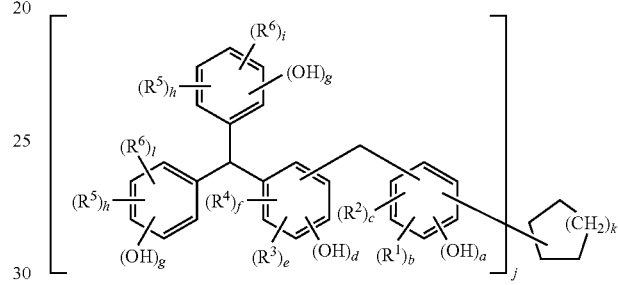

(I)

[wherein, R$^1$ to R$^6$ each represent, independently, an alkyl group of 1 to 10 carbon atoms or an aromatic hydrocarbon group, which may include a hetero atom within a structure thereof; a represents an integer of 1 or greater, and b and c each represent, independently, either 0 or an integer of 1 or greater, provided that at least one of b or c is an integer of 1 or greater, and a+b+c is no greater than 4; d represents an integer of 1 or greater, and e and f each represent, independently, either 0 or an integer of 1 or greater, provided that d+e+f is no greater than 4; g represents an integer of 1 or greater, and h and i each represent, independently, either 0 or an integer of 1 or greater, provided that at least one of h or i is an integer of 1 or greater, and g+h+i is no greater than 4; j represents 2; and k represents an integer from 1 to 3];

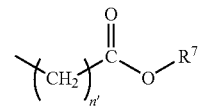

(II)

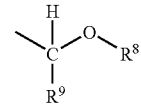

(III)

[wherein, R$^7$ and R$^8$ each represent, independently, a straight-chain, branched, or cyclic alkyl group, which may include a hetero atom within a structure thereof; R$^9$ represents a hydrogen atom or a lower alkyl group; and n' represents an integer from 1 to 3].

2. A positive resist composition according to claim 1, further comprising a nitrogen-containing organic compound (D).

3. A method for forming a resist pattern, comprising the steps of:
   forming a resist film on a substrate using a positive resist composition according to claim 2;

conducting exposure of said resist film; and
developing said resist film to form a resist pattern.

4. A method for forming a resist pattern, comprising the steps of:
forming a resist film on a substrate using a positive resist composition according to claim 1;
conducting exposure of said resist film; and
developing said resist film to form a resist pattern.

5. A compound, wherein either a portion of, or all of, hydrogen atoms of phenolic hydroxyl groups within a polyhydric phenol compound with a molecular weight of 300 to 2,500 represented by a general formula (I) shown below have been substituted with at least one group selected from the group consisting of acid-dissociable, dissolution-inhibiting groups represented by a general formula (II) shown below and acid-dissociable, dissolution-inhibiting groups represented by a general formula (III) shown below:

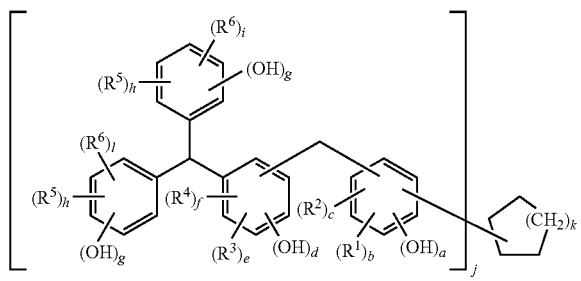
(I)

[wherein, $R^1$ to $R^6$ each represent, independently, an alkyl group of 1 to 10 carbon atoms or an aromatic hydrocarbon group, which may include a hetero atom within a structure thereof; a represents an integer of 1 or greater, and b and c each represent, independently, either 0 or an integer of 1 or greater, provided that at least one of b or c is an integer of 1 or greater, and a+b+c is no greater than 4; d represents an integer of 1 or greater, and e and f each represent, independently, either 0 or an integer of 1 or greater, provided that d+e+f is no greater than 4; g represents an integer of 1 or greater, and h and i each represent, independently, either 0 or an integer of 1 or greater, provided that at least one of h or i is an integer of 1 or greater, and g+h+i is no greater than 4; j represents 2; and k represents an integer from 1 to 3];

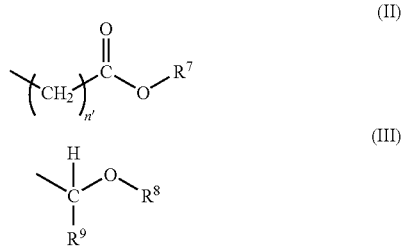

[wherein, $R^7$ and $R^8$ each represent, independently, a straight-chain, branched, or cyclic alkyl group, which may include a hetero atom within a structure thereof; $R^9$ represents a hydrogen atom or a lower alkyl group; and n' represents an integer from 1 to 3].

* * * * *